United States Patent
Miller et al.

(10) Patent No.: US 6,426,362 B1
(45) Date of Patent: Jul. 30, 2002

(54) FORMULATIONS OF TOCOPHEROLS AND METHODS OF MAKING AND USING THEM

(75) Inventors: Guy Miller, Mountain View; Lesley A. Brown, Cupertino, both of CA (US)

(73) Assignee: Galileo Laboratories, Inc., Santa Clara, CA (US)

( * ) Notice: Subject to any disclaimer, the term of this patent is extended or adjusted under 35 U.S.C. 154(b) by 0 days.

(21) Appl. No.: 09/684,588

(22) Filed: Oct. 6, 2000

Related U.S. Application Data

(60) Provisional application No. 60/158,234, filed on Oct. 8, 1999.

(51) Int. Cl.$^7$ .................. A61K 31/35; A61K 31/38; A61K 31/355
(52) U.S. Cl. .................. 514/458; 514/456; 514/457
(58) Field of Search ................ 574/456, 457; 574/458, 27

(56) References Cited

U.S. PATENT DOCUMENTS

| | | | |
|---|---|---|---|
| 4,977,282 A | 12/1990 | Baldwin et al. | |
| 4,978,617 A | 12/1990 | Furuya | |
| 5,043,323 A | 8/1991 | Bombardelli et al. | |
| 5,114,957 A | 5/1992 | Hendler et al. | |
| 5,235,073 A | 8/1993 | Kim et al. | |
| 5,504,220 A | 4/1996 | Kuo et al. | |
| 5,587,176 A | 12/1996 | Warren et al. | |
| 5,606,080 A | 2/1997 | Ogata et al. | |
| 5,652,274 A | 7/1997 | Martin | |
| 5,733,926 A | 3/1998 | Gorbach | |
| 5,741,957 A | 4/1998 | Deboer et al. | |
| 5,744,957 A | 4/1998 | Vaughan, Jr. | |
| 5,763,414 A | 6/1998 | Bok et al. | |
| 5,801,159 A | 9/1998 | Miller et al. | |
| 5,804,555 A | * 9/1998 | Tomita et al. ................. 514/12 |
| 5,858,371 A | 1/1999 | Singh et al. | |
| 5,952,374 A | 9/1999 | Clarkson, Jr. et al. | |
| 5,972,993 A | * 10/1999 | Ptchelintsev et al. ....... 514/449 |
| 6,048,891 A | 4/2000 | Wechter | |
| 6,083,982 A | 7/2000 | Wechter et al. | |
| 6,103,756 A | * 8/2000 | Gorsek ........................ 514/458 |
| 6,150,402 A | 11/2000 | Wechter et al. | |
| 6,180,662 B1 | * 1/2001 | Lanzedorfer et al. ....... 514/456 |
| 6,242,479 B1 | 6/2001 | Wechter | |

OTHER PUBLICATIONS

"Antioxidant activity of quercetin against metmyoglobin–induced oxidation of fish oil–bile salt emulsion", Hoshino et al., Biosci., Biotechnol., biochem., 1997, 61(10), 1634–1640, abstract.*
"Effects of alpha–tocopherol on the protective effects of flavonoids against cytotocitiy of lipperoxides", Kaneko et al, Bitamin E Kenkyu no Shinpo, 1998, 8, 215–221, abstract.*
"UC Berkeley and Australian researchers call into question current formulation of Vitamin E supplements", Robert Sanders, News Release (www.berkeley.edu), 1997.*
"Scientific Study–Tocotrienol & Breast Cancer", Guthrie et al., Asia Pacific J Clin Nutr, 1997, 6(1):41–45.*
Ambruso, Daniel R. and Johnston, Jr., Richard B. (1981). "Lactoferrin enhances hydroxyl radical production by human neutrophils, neutrophil particulate fractions, and an enzymatic generating system" *J. Clin. Invest.* 67:352–360.
Amiel, M. and Barbe, R. (1998). "Etude de l'activité pharmacodynamique de daflon 500 mg" *Ann. Cardiol. Angéiol.* 47(3):185–188. (English summary).
Arnold, Roland R. et al. (1977). "A bacterial effect for human lactoferrin" *Science* 197:263–265.
Arora, Arti et al. (1998). "Antioxidant activities of isoflavones and their biological metabolites in a liposomal system" *Arch Biochem. Biophys.* 356(2):133–141.
Bouskela, E. et al. (1995). "Effects of daflon 500 mg on increased microvasular permeability in normal hamsters" *Int. J. Microcirc.* 15 (suppl. 1):22–26.
Boveris, Alberto and Chance, Britton (1973). "The mitochondrial generation of hydrogen peroxide" *Biochem. J.* 134:707–716.
Britigan, Bradley E. et al. (1994). "The role of lactoferrin as an anti–inflammatory molecule" *Adv. Exp. Med. Biol.* 357:143–156.
Ciolino, Henry P. et al. (1998). "Diosmin and diosmetin are agonists of the aryl hydrocarbon receptor that differentially affect cytochrome P450 1A1 activity" *Cancer Res.* 58:2754–2760.
de Boer J. et al. (1999). "A randomized multicenter study on kidney preservation comparing HTK with UW" *Transplantation Proceedings* 31:2065–2066.
Delbarre, B. et al. (1995). "Effect of daflon 500 mg, a flavonoid drug, on neurological signs, levels of free radicals and electroretinogram in the gerbil after ischemia–reperfusion injury" *Int. J. Microcirc.* 15 (suppl. 1):27–33.
Diplock, A.T. et al. (1998). "Functional food science and defence against reactive oxidative species" *Br. J. Nutr.* 80(suppl. 1):S77–S112.
Dumon, M. F. et al. (1994). "Mise en évidence de l'effet antilipoperoxydant du 7 rutinoside de la 3',5, 7–trihydroxy–4'–methoxy flavone: étude in vitro" *Ann. Biol. Clin.* 52: 265–270. (English summary.).

(List continued on next page.)

Primary Examiner—Zohreh Fay
Assistant Examiner—Brian-Yong Kwon
(74) Attorney, Agent, or Firm—Morrison & Foerster LLP

(57) ABSTRACT

Non-naturally-occuring compositions for use in amelioration of disruption of energy metabolism secondary to stress are described. The compositions comprise a tocopherol and/or a derivative thereof, and a synergist, and are particularly suited for use as nutritional supplements. Synergists include, but are not limited to, flavonoids and lactoferrin and/or derivatives thereof. Compositions comprising an optimized formulation comprising a tocopherol and an additional compound such as daidzein or biochanin A are also described. Methods of making these compositions and methods of ameliorating injury(ies) or disruption of energy metabolism secondary to stress, comprising administering such compositions, are also disclosed.

22 Claims, No Drawings

OTHER PUBLICATIONS

Elwatidy, Ahmed M.F. et al. (1999). "Antegrade crystalloid cardioplegia vs antegrade/retrograde cold and tepid blood cardioplegia in CABG" *Ann. Thorac. Surg.* 68:447–453.

Fleet, James C. (1995). "A new role for lactoferrin: DNA binding and transcription activation" *Nutrition Rev.* 53(8):226–227.

Freneix–Clerc, M. et al. (1994). "Etude in vivo de l'effet antilipoperoxydant du 7 rutinoside de la 3',5, 7–trihydroxy–4'–methoxy flavone" *Ann. Biol. Clin.* 52:171–177. (English summary.).

Friesenecker, B. et al. (1995). "Cellular basis of inflammation, edema and the activity of daflon 500 mg" *Int. J. Microcirc.* 15 (suppl. 1):17–21.

Fukuzawa, Kenji et al. (1982). "Antioxidant activities of tocopherols on $Fe^{2+}$–ascorbate–induced lipid peroxidation in lecithin liposomes" *Lipids* 17(7):511–513.

Gebicki, Silvia and Gebicki, Janusz M. (1999). "Crosslinking of DNA and proteins induced by protein hydroperoxides" *Biochem. J.* 338:629–636.

Guidot, David M. et al. (1995). "Mitochondrial respiration scavenges extramitochondrial superoxide anion via a non-enzymatic mechanism" *J. Clin. Invest.* 96:1131–1136.

Guillot, R. et al. (1998). "Effect of long–term treatment with a purified micronized flavonoid fraction on pancreatic mononuclear cell infiltration in diabetic BB rats" *Pancreas* 17(3):301–308.

Guthrie, N. and Carroll, K.K. (1998). "Inhibition of mammary cancer by citrus flavonoids" *Adv. Exp. Med. Biol.* 439:227–236.

Halliwell, Barry et al. (1992). "Interaction of nitrogen dioxide with human plasma: Antioxidant depletion and oxidative damage" *FEBS Lett.* 313(1):62–66.

Halliwell, Barry (1996). "Antioxidants in human health and disease" *Ann. Rev. Nutr.* 16:33–50.

Hammons, George J. et al. (1999). "Effects of chemoprotective agents on the metabolic activation of the carcinogenic arylamines PhIP and 4–aminobiphenyl in human and rat liver microsomes" *Nutrition and Cancer* 33(1):46–52.

Hermes–Lima, Marcelo et al. (1995). "Characteristics of Fe (II)ATP complex–induced damage to the rat liver mitochondrial membrane" *Mol. Cell. Biochem.* 145:53–60.

Hodgson, Jonathan M. et al. (1999). "Isoflavonoids do not inhibit in vivo lipid peroxidation in subjects with high–normal blood pressure" *Atherosclerosis* 145:167–172.

Jenkinson, Stephen G. (1989). "Free radical effects on lung metabolism" *Clin. Chest Med.* 10(1):37–47.

Kavutcu, M. and Melzig, M. F. (1999). "In vitro effects of selected flavonoids on the 5'–nucleotidase activity" *Pharmazie* 54:457–459.

Kowaltowski, Alicia J. et al. (1995). "$CA^{2+}$–induced mitochondrial membrane permeabilization: role of coenzyme Q redox state" *Am. J. Physiol.* 269:C141–C147.

Kowaltowski, Alicia J. et al. (1996). "Effect of inorganic phosphate concentration on the nature of inner mitochondrial membrane alterations mediated by $Ca^{2+}$ ions" *J. Biol. Chem.* 271(6):2929–2934.

Kowaltowski, Alicia J. et al. (1998). "Activation of the potato plant uncoupling mitochondiral protein inhibits reactive oxygen species generation by the respiratory chain" *FEBS Letters* 425:213–216.

Leth, Torben and Søndergaard, Helge (1977). "Biological activity of vitamin E compounds and natural materials by the resorption–gestation test, and chemical determination of the vitamin E activity in foods and feeds" *J. Nutr.* 107:2236–2243.

Levay, Peter Ferenc and Viljoen, Margaretha (1995). "Lactoferrin: A general review" *Haematologica* 80:252–267.

Liu, Shirley X.L. et al. (1996). "Increase of ocular blood flow by some phytogenic compounds" *J. Ocul. Pharm.Ther.* 12(2):95–101.

Liu, Shu–sen (1997). "Generating, partitioning, targeting and functioning of superoxide in mitochondria" *Biosc. Rep.* 17(3):259–272.

Lönnerdal, B. and Iyer, S. (1995). "Lactoferrin: Molecular structure and biological function" *Ann. Rev. Nutr.* 15:93–110.

Lyn–Cook, Beverly D. et al. (1999). "The effects of phytoestrogens on human pancreatic tumor cells in vitro" *Cancer Lett.* 142:111–119.

Matsuda, Naruto et al. (1999). "Influence of oxygenation on endothelial modulation of coronary vasomotor function during hyperkalemic cardioplegia" *Surgery* 126(2):264–271.

Melzig, M. F. and Loose, R. (1999). "Inhibition of lipopolysaccharide (LPS)–induced endothelial cytotoxicity by diosmin" *Pharmazie* 54:298–299.

Minotti, Giorgio and Aust, Steven D. (1987). "An investigation into the mechanism of citrate–$Fe^{2+}$–dependent lipid peroxidation" *Free Radic. Biol. Med.* 3:379–387.

Moon, Ja–Young et al. (1998). "Inhibition of 7–ethoxycoumarin 0–deethylase activity in rat liver microsomes by naturally occurring flavonoids: structure–activity relationships" *Xenobiotica* 28(2):117–126.

Mühlbacher, F. et al. (1999). "Preservation solutions for transplantation" *Transplant Proc.* 31:2069–2070.

Neuzil, Jiri and Baoutina, Anna (1998). "α–tocopherol in atherogenesis: Do we know its real role?" *Cardiovasc. Drugs Ther.* 12:421–423.

Nolte, D. et al. (1997). "Effects of Daflon® 500 $mg^1$ on postischemic macromolecular leak syndrome in striated skin muscle of the hamster" *Int. J. Microcirc.* 17 (suppl. 1):6–10.

Packer, L. et al. (1999). "Antioxidant activity and biologic properties of a procyanidin–rich extract from pine (*pinus maritima*) bark, pycogenol" *Free Radic. Biol. Med.* 27(5/6):704–724.

Reiter, Russel J. et al. (1998). "Reactive oxygen intermediates, molecular damage, and aging" *Ann. N.Y. Acad. Sci.* 854:410–424.

Saija, Antonella et al. (1995). "Flavonoids as antioxidant agents: Importance of their interaction with biomembranes" *Free Radic. Biol. Med.* 19(4):481–486.

Saini, T. et al. (1998). "Protective ability of acetylsalicyclic acid (aspirin) to scavenge radiation induced free radicals in J774A.1 macrophage cells" *Res. Comm. Mol. Pathol. Pharmacol.* 101(3):259–268.

Sánchez, Lourdes et al. (1992). "Biological role of lactoferrin" *Arch. Dis. Child.* 67:657–661.

So, Felicia V. et al. (1997). "Inhibition of proliferation of estrogen receptor–positive MCF–7 human breast cancer cells by flavonoids in the presence and absence of excess estrogen" *Cancer Lett.* 112:127–133.

Soukka, Tero et al. (1992). "Fungicidal effect of human lactoferrin against *Candida albicans*" *Microbiol. Lett.* 90:223–238.

Spik, Geneviève et al., eds., (1998). *Advances in Lactoferrin Research,* Plenum Press, New York, pp. ix–xiii (Table of Contents).

Tangerås, Arild et al. (1980). "Mitochondrial iron not bound in heme and iron–sulfur centers: Estimation, compartmentation and redox state" *Biochem. Biophys. Acta* 589:162–175.

Tanoue, Y. et al. (1998). "Arresting donor hearts with extracellular–type cardioplegia prevents vasoconstriction induced by US solution" *Cardiovasc. Surg.* 6(6):622–628.

Teel, Robert W. and Huynh, Huong (1998). "Modulation by phytochemicals of cytrochrome P450–linked enzyme activity" *Cancer Lett.* 133:135–141.

'T Hart, Bert A. et al. (1990). "How flavonoids inhibit the generation of luminol–dependent chemiluminescence by activated human neutrophils" *Chem. Biol. Interactions* 73:323–335.

Toda, Shizuo and Shirataki, Yoshiaki (1999). "Inhibitory effects of isoflavones on lipid peroxidation by reactive oxygen species" *Phytother. Res.* 13:163–165.

Tomita, Mamoru et al. (1994). "A review: The active peptide of lactoferrin" *Acta Paed. Japonica* 36:585–591.

Traber, Maret G. and Packer, Lester (1995). "Vitamin E. beyond antioxidant function" *Am. J. Clin. Nutr.* 162(suppl):1501S–1509S.

Turrens, Julio F. (1997). "Superoxide production by the mitochondrial respiratory chain" *Bioscience Reports* 17(1)3–8.

Unruh, Helmet W. (1995). "Lung preservation and lung injury" *Chest Surg. Clin. N. Am.* 5(1):91–106.

Vento, Antti E. et al. (1999). "Nitecapone as an additive to crystalloid cardioplegia in patients who had coronary artery bypass grafting" *Ann. Thorac. Surg.* 68:413–420.

Watabe, Shoji et al. (1997). "SP–22 is a thioredoxin–dependent peroxidase reductase in mitochondria" *Eur. J. Biochem.* 249:52–60.

Wechter, William J. et al. (1996). "A new endogenous natriuretic factor: LLU–α" *Proc. Nat. Acad. Sci.* 93:6002–6007.

Wieselthaler, G. M. et al. (1999). "Improved graft function using a new myocardial preservation solution: Celsior. Preliminary data from a randomized prospective study" *Transplant Proc.* 31:2067–2068.

Yin, Fen et al. (1999). "Growth inhibitory effects of flavonoids in human thyroid cancer cell lines" *Thyroid* 9(4):369–376.

Zhao, W. et al. (1996). "Neuroprotective effects of hypothermia and U–78517F in cerebral ischemia are due to reducing oxygen–based free radicals: An electron paramagnetic resonance study with gerbils" *J. Neurosci. Res.* 45:282–288.

* cited by examiner

FORMULATIONS OF TOCOPHEROLS AND METHODS OF MAKING AND USING THEM

CROSS-REFERENCE TO RELATED APPLICATIONS

This application claims the benefit of U.S. Provisional Application No. 60/158,234 filed Oct. 8, 1999, which is hereby incorporated herein in its entirety by reference.

STATEMENT OF RIGHTS TO INVENTIONS MADE UNDER FEDERALLY-SPONSORED RESEARCH

This invention was made in part during work supported by a grant from the Office of Naval Research N00014-98-C-0139. The government has certain rights in the invention.

TECHNICAL FIELD

This invention generally relates to non-naturally-occurring nutritional compositions for amelioration of disruption of energy metabolism secondary to stress comprising a tocopherol and/or a derivative thereof, and a synergist in effective amounts. The synergist can include a flavonoid, such as hesperetin, diosmin, combinations of such flavonoids or lactoferrin and/or derivatives thereof. Synergistic combinations of different forms of tocopherol, such as alpha- and gamma-tocopherol exemplified herein, also form a part of the present invention.

The invention also relates to non-naturally-occurring compositions comprising optimized formulations for amelioration of disruption of energy metabolism secondary to stress comprising a tocopherol and/or a derivative thereof, and an additional compound such as one or more flavonoids, exemplified by daidzein or biochanin A in effective amounts, empirically determined ratios of other flavonoids, other tocopherols, or lactoferrin, as exemplified herein. The invention also elates to methods of making such compositions.

BACKGROUND OF THE INVENTION

Metabolic pathways are of two types: anabolic, which are involved in synthetic work and require energy; and catabolic, which are degradative and energy-releasing. Catabolic and anabolic pathways can share a common partial sequence, which functions in one direction for synthesis and in the opposite direction for degradation. However, one route is never exactly the reverse of the other, since both need to be exergonic in their respective directions. For example, the pathways for glucose synthesis (gluconeogenesis) and glucose degradation (glycolysis) share many reactions in common, but each have several unique steps. These unique steps generally ensure thermodynamic irreversibility and can serve as regulatory sites. In the catabolic pathways, a substrate is sequentially degraded, releasing energy in the form of ATP (adenosine triphosphate). Catabolic pathways include both the anaerobic pathway, (i.e., fermentation) and the aerobic pathway (i.e., oxidative metabolism or respiration). For reviews, see Atkinson (1977) *Cellular Energy Metabolism and Its Regulation,* Academic Press, New York; Hochachka et al. (1993) *Surviving Hypoxia: Mechanisms of Control and Adaptation,* CRC Press, Inc., Fl.; and Alberts et al. (1994) *Molecular Biology of the Cell,* Garland Publ., New York. While metabolic pathways produce ATP, an essential energy carrier, by-products of these pathways include free radicals, which are potent cellular injurants.

Reactive oxygen species (ROS), also designated free radicals, include among other compounds singlet oxygen, the superoxide anion ($O_2.-$), nitric oxide (NO.), and hydroxyl radicals. Mitochondria are particularly susceptible to damage induced by ROS, as these are generated continuously by the mitochondrial respiratory chain. See, for example, Boveris et al. (1973) *Biochem. J.* 134:707–716; Turrens et al. (1997) *Biosc. Rep.* 17:3–8; Tangeras et al. (1980) *Biochim. Biophys. Acta* 589:162–175; Minotti et al. (1987) *Free Radic. Biol. Med.* 3:379–387; Hermes-Lima et al. (1995) *Mol. Cell. Biochem.* 145:53–60; Liu et al. (1997) *Biosc. Rep.* 17:259–272; Kowaltowski et al. (1998) *FEBS Letters* 425:213–216; Kowaltowski et al. (1995) *Am. J. Physiol.* 269:C141–147; Kowaltowski et al. (1996) *J. Biol. Chem.* 271:2929–2934. Free radicals attack membrane lipids and lipoproteins, generating carbon radicals. These in turn react with oxygen to produce a peroxyl radical, which may attack adjacent fatty acids to generate new carbon radicals. This process can lead to a chain reaction producing lipid peroxidation products. Halliwell (1994) *Lancet* 344:721–724. Damage to the cell membrane can result in loss of cell permeability, increased intercellular ionic concentration, and/or decreased ability to excrete or detoxify waste products. The peroxynitrite anion ($ONOO^-$), a reaction product of $O_2.^-$ and nitric oxide (NO.) (Pryor et al. (1995) *Am J. Physiol.* 268:699–722), appears to be responsible for many effects previously attributed to NO. Castro et al. (1994) *J. Biol. Chem.* 269:29409–29415; Ischiropoulos et al. (1992) *Arch. Biochem. Biophys.* 2:446–453; Halliwell et al. (1995) *Ann. Rheumat. Dis.* 54:505–510; Salvemini et al. (1996a) *Br. J. Pharmacol.* 118:829–838; Salvemini et al. (1996b), *Eur. J. Pharmacol.* 303:217–220; Cuzzocrea et al. (1998) *Free Radic. Biol. Med.* 24:450–459; Wizemann et al. (1994) *J. Leukoc. Biol.* 56:759–768; Szabo et al. (1997) *J. Clin. Invest.* 100:723–735. ROS can also contribute to damage to organs and organisms levels. These conditions include cell aging, as well as inflammation and cancer.

Free radicals are also problematic in organ transplantation, during which process cells and tissues experience hypoxia. After transplantation, the grafted tissue is reperfused with oxygenated blood. When reperfusion occurs and the flow of oxygen is restored, a burst of free radicals forms. The accumulation of free radicals contributes to post-transplantation injury in tissue giving rise to an increased number of damaged cells and an enhanced immune response by the recipient host. Zhao et al. (1996) *J. Neurosci. Res.* 45:282–288; Unruh (1995) *Chest Surg. Clin. N. Am.* 5:91– 106. This immune response can lead to inflammation and reduced function in the transplanted tissue and/or rejection and failure of the graft.

Production of ROS also increases when cells experience a variety of stresses, including organ ischemia and reperfusion (as described above) and ultraviolet light exposure and other forms of radiation. Reiter et al. (1998) *Ann. N. Y. Acad. Sci.* 854:410–424; Saini et al. (1998) *Res. Comm. Mol Pathol Pharmacol.* 101:259–268; Gebicki et al. (1999) *Biochem. J.* 338:629–636. ROS are also produced in response to cerebral ischemia, including that caused by stroke, traumatic head injury and spinal injury. In addition, when metabolism increases or a body is subjected to extreme exercise, the endogenous antioxidant systems are overwhelmed, and free radical damage can take place. Free radicals are reported to cause the tissue-damage associated with some toxins and unhealthful conditions, including toxin-induced liver injury. Obata (1997) *J. Pharm. Pharmacol.* 49:724–730; Brent et al. (1992) *J. Toxicol. Clin. Toxicol.* 31:173–196; Rizzo et al. (1994) *Zentralbl. Veterinarmed.* 41:81–90; Lecanu et al. (1998) *Neuroreport* 9:559–663. Exposure to hyperoxia also results in free-radical production, which can lead to lung damage if not counteracted by sufficient levels of antioxidants. Jenkinson (1989) *Clin. Chest Med.* 10:37–47. Free radicals may also be responsible for freezing stress in plants. Tao et al. (1998) *Cryobiology* 37:38–45.

In addition to stresses described above, cells are subject to other stresses, including hyper- and hypothermia, infection, osmotic, hyper- and hypo-gravity, starvation, growth in various reactors (such as bioreactors, fermentation, food preparation, etc.), toxicity (e.g., inhalation of toxic gases such as HCN, phosphates, thiophosphates), drug overdoses, and the like. Common to many of these stresses are injuries secondary to disruptions in energy metabolism. Treatment of these types of injuries includes administration of various individual or combinations of tocopherols which protect against disruptions of energy metabolism and the resulting cell injury during stress ("cytoprotectants"). For example, the time that mammalian cells can undergo stress induced energy dysfunction stress be extended by administration of purine derivatives, alone or in combination with electron acceptor compounds and/or amino acids. U.S. Pat. No. 5,801,159.

Because of the potentially damaging nature of free radicals, and because $O_2^-$ generation is continuous, the body has a number of antioxidant defense mechanisms including enzymes, such as vitamin E, vitamin C, superoxide dismutase, catalase, glutathione peroxidase, glutathione reductase, NADP transhydrogenase, thiol peroxidase SP-22, copper and iron transport, storage proteins, water-soluble and lipid-soluble molecular antioxidants, glutathione, NADPH and mitochondrial respiration. Watabe et al. (1997) *Eur. J Biochem.* 249:52–60; Guidot et al. (1995) *J. Clin. Invest.* 96:1131–1136, Radi et al. (1991) *J. Biol. Chem.* 261:14081–14024. Superoxide radicals produced by the respiratory chain are readily dismutated by mitochondrial superoxide dismutase (MnSOD), leading to the production of $H_2O_2$. Fridovich et al. (1997) *J. Biol. Chem.* 272:18515–18517.

Vitamin E (alpha-tocopherol) and closely related compounds have been hypothesized thought to act as antioxidants. Halliwell (1996) *Ann. Rev. Nutr.* 16:33–50; Diplock et al. (1998) *Br. J. Nutr.* 80: S77–112. Alpha-tocopherol can prevent lipid peroxidation in vitro, and this function can be replaced by known antioxidants. However, additional functions for vitamin E seem likely, since other antioxidants cannot relieve all the symptoms of vitamin E deficiency. There is increasing evidence that tocopherols are involved in the control of cell proliferation and differentiation. Traber et al. (1995) *Am. J Clin. Nutr.* 62: 1501S–1509S. Alpha-tocopherol also functions as a scavenger of active nitrogen species [Halliwell et al. (1992) *FEBS Lett.* 313:62–66] and a gamma-tocopherol metabolite is a natriuretic [Wetchter et al. (1996) *Proc. NatL Acad. Sci. USA* 93:6002–6007; U.S. Pat. No. 6,048,891, incorporated herein by reference]. In addition, alpha-tocopherol or its quinone derivatives may be involved in fatty acid desaturation. Infante (1986) *Mol. Cell. Biochem.* 69:93–108; Infante et al. (1998) *FEBS Lett.* 431:1–6. An additional major role of dietary alpha-tocopherol may be as a precursor of its D-alpha-tocopherolquinone metabolite whose semiquinone radical is required as an essential enzyme cofactor by carnitine-dependent, channeled mitochondrial fatty acid desaturases. Infante (1999) *FEBS Lett.* 446:1–5.

Tocopherols, while generally similar in overall chemical structure, vary widely and unpredictably in biological function. Alpha-tocopherol is generally considered the most biologically active form of vitamin E; it is also the most abundant in adult human serum. Neuzil et al. (1998) *Card. Drugs. Ther.* 12:421–423; Strohschein et al. (1998) *Anal. Chem.* 70:13–18; Gonzalez (1990) *Med. Hypothes.* 32:107–110. Alpha-tocopherol has a greater antioxidant activity than the other tocopherols. Fukuzawa et al. (1982) *Lipids* 17:511–13. D-alpha-tocopherol sometimes shows a greater efficacy than d,l-alpha tocopherol (mixed racemic mixture, also referred to as +/−alpha-tocopherol). Leth et al. (1977) *J. Nutr.* 107: 2236–2243. Alpha-tocopherol, but not beta-tocopherol, inhibits protein kinase C function. Ricciarelli et al. (1998) *Biochem. J.* 334:243–249. However, both alpha- and beta-tocopherol inhibit porcine pancreatic phospholipase A2 activity. Grau et al. (1998) *Chem. Phys. Lipids* 91:109–118. Alpha-, beta-, gamma- and delta-tocopherol were all able to inhibit superoxide generation by neutrophils. Kanno et al. (1996) *Free Radic. Res.* 24:181–189. Delta-tocopherol has only one hundredth of the activity of natural alpha-tocopherol in the Evans resorption sterility test for vitamin E. The role of vitamin E in treating coronary heart disease is complex; the results of studies on this topic have been confusing and sometimes seemingly contradictory. Neuzil et al. (1998) *Cardiovasc. Drugs. Ther.* 12:421–3.

Common to many of the stresses described herein are injuries secondary to disruptions in energy metabolism. The need remains for identification of effective, novel formulations and combinations of compounds which aid in the survival and recovery of cells during injury secondary to stress and disruption of energy metabolism.

SUMMARY OF THE INVENTION

In one embodiment, the invention relates to non-naturally-occurring compositions or formulations for amelioration of disruption of energy metabolism secondary to stress comprising a tocopherol selected from the group consisting of alpha-, delta- and gamma-tocopherol and combinations or derivatives thereof, and a synergist selected from the group consisting of lactoferrin, a flavonoid, such as hesperetin or diosmin, and a combination of flavonoids, including derivatives thereof, wherein the tocopherol and the synergist are present in amounts effective to ameliorate stress responses in cells. Such compositions or formulations are particularly useful as nutritional supplements.

In another embodiment, the invention relates to non-naturally-occurring compositions comprising an optimized formulation for amelioration of disruption of energy metabolism secondary to stress comprising a tocopherol and combinations or derivatives thereof, and an additional compound selected from the group consisting of a flavonoid, such as daidzein, biochanin A, or a combination of flavonoids or a derivative thereof, wherein the tocopherol and the additional compound are present in amounts effective to ameliorate stress responses in cells. In one embodiment, the optimized formulation comprises an alpha-tocopherol or derivative thereof and daidzein or derivative thereof. In another embodiment, the invention relates to a method for amelioration of disruption of energy metabolism secondary to stress, comprising administering such a composition to a subject. In another embodiment, the invention encompasses a method of making such a composition.

In various embodiments, the tocopherol is alpha-, delta- or gamma-tocopherol. The composition can also comprise a mixture of tocopherols, such as structurally distinct tocopherols, or stereoisomers. The tocopherol can be in the form of a pharmaceutically acceptable salt.

In various embodiments, the stress can be induced by an environmental alteration, chemical insult or physiological condition. Environmental alterations include, but are not limited, to hypothermia, hyperthermia, hypoxia, and ionizing radiation. Chemical insults include, but are not limited to, drug toxicity, chemotherapy, exposure to at least one toxin, and cell culture. Physiological conditions include, but are not limited to, physical exertion, aging, disease and pre-surgical and post-surgical situations.

In various embodiments, the invention also relates to methods of making these compositions comprising adding a tocopherol or derivative thereof to a synergist, daidzein or biochanin A or derivative thereof, in sufficient amounts to ameliorate stress.

In various embodiments, the invention also relates to methods for the amelioration of disruption of energy metabolism secondary to stress, comprising administering to a subject such a composition.

BRIEF DESCRIPTION OF FIGURES (Not applicable.)

Modes for Carrying Out the Invention

It would be highly advantageous to obtain new non-naturally-occurring compositions comprising cytoprotective agents for amelioration of disruption of energy metabolism secondary to stress. It would also be advantageous to obtain new methods of ameliorating disruption of energy metabolism secondary to stress comprising administering such compositions. In addition, it would be further advantageous to obtain new methods of making such compositions. The compositions comprise a tocopherol or tocopherol derivative and a synergist such as a flavonoid (e.g.,. hesperetin,, diosmin or derivatives or combinations thereof), or lactoferrin or a derivative thereof.

In another embodiment, the composition can comprise an optimized formulation for amelioration of disruption of energy metabolism. Such compositions are combinations of compounds in amounts determined or predicted to be particularly effective to ameliorate disruption of energy metabolism secondary to stress, as described herein. In optimized formulations, the combined amounts of the component compounds are selected to increase, augment or enhance the cytoprotective effect of either agent when used individually at the same concentration. In particular, optimized formulations exemplified herein, which form part of the present invention, include a tocopherol or tocopherol derivative and an additional flavonoid compound such as daidzein or biochanin A, or a combination of such flavonoid compounds, or a lactoferrin One exemplary optimized formulation comprises alpha-tocopherol or (+/−)-alpha-tocopherol and daidzein.

Definitions

By "non-naturally-occurring composition" is meant a composition which is not found in this form in nature. A non-naturally-occurring composition can be derived from a naturally-occurring composition, e.g., as non-limiting examples, via purification, isolation, concentration, chemical modification (e.g., addition or removal of a chemical group), and/or, in the case of mixtures, addition or removal of ingredients or compounds. Alternatively, a non-naturally-occurring composition can comprise or be derived from a non-naturally-occurring combination of naturally-occurring compositions. Thus, a non-naturally-occurring composition can comprise a mixture of purified, isolated, modified and/or concentrated naturally-occurring compositions, and/or can comprise a mixture of naturally-occurring compositions in forms, concentrations, ratios and/or levels of purity not found in nature.

"Agents" or "cytoprotective agents" are defined herein as compounds, mixtures, or formulations of compounds which are capable of amelioration of symptoms of stress and/or injury(ies) and disruption of energy metabolism secondary to-stress. "Amelioration" means the prevention, reduction or palliation of a state. Cytoprotective agents may provide cytoprotective activity prior to, simultaneous with and/or after disruption of energy metabolism.

As used herein, an agent is said to be "cytoprotective" or to have "cytoprotective property" or "cytoprotective activity" if administration of the agent ameliorates symptoms of stress and/or injury(ies) suffered by cells, tissues, organs and/or organisms that is induced secondary to disruption of energy metabolism. Cytoprotective activity and injury can be quantified in assays which measure results of injury such as death and inhibition of metabolic activity; these can be measured, for example, using appropriate fluorescent dyes or measuring enzyme activity and/or measuring intact cellular membranes in affected tissues by staining with appropriate indicators. Cytoprotective agents include cytoprotective tocopherols and combinations comprising a tocopherol.

By "tocopherol" is meant any of a family of molecules (including both tocopherols and tocotrienols and derivatives thereof) which are characterized by a 6-chromanol ring structure and a side chain at the 2 position. Tocopherols possess a 4',8',12'-trimethyltridecyl phytol side chain, and the tocotrienols differ by the presence of double bonds at the 3', 7' and 11' positions of the side chain. As used herein, the term "tocopherol" encompasses, but is not limited to:

alpha-tocopherol (vitamin E), [2R-2R*(4R*,8R*)]-3,4-dihydro-2,5,7,8-tetramethyl-2-(4,8,12-trimethyltridecyl)-2H-1-benzopyran-6-ol; 2,5,7,8-tetramethyl-2-(4',8',12'-trimethyltridecyl)-6-chromanol; 5,7,8-trimethyltocol, Fernholz (1937) *J. Am. Chem. Soc.* 59:1154 and 60:700;

beta-tocopherol, 3,4-dihydro-2,5,8-trimethyl-2-(4,8,12-trimethyltridecyl)-2H-1-benzopyran-6-ol; 2,5,8-trimethyl-2-(4,8,12-trimethyltridecyl)-6-chromanol; 5-8-dimethyltocol; cumotocopherol; neotocopherol; p-xylotocopherol;

gamma-tocopherol, 3,4-dihydro-2,7,8-trimethyl-2-(4,8,12-trimethyltridecyl)-2H-1-benzyopyran-6-ol; 2,7,8-trimethyl-2-(4,8,12-trimethyltridecyl)-6-chromanol; 7,8-dimethyltocol; o-xylotocopherol;

delta-tocopherol, [2R-[2R*(4R*,8R*)]]-3,4-dihydro-2,8-dimethyl-2-(4,8,12-trimethyltridecyl)-2H-1-benzopyran-6-ol; 8-methyltocol;

epsilon-tocopherol, [R-(E,E)]-3,4-dihydro-2,5,8-trimethyl-2-(4,8,12-trimethyl-3,7,11-tridecatrienyl)-2H-1-benzopyran-6-ol; 2,5,8-trimethyl-2-(4,8,12-trimethyltrideca-3,7,11-trienyl)chroman-6-ol; 5-methyltocol;

$zeta_1$-tocopherol, 3,4-dihydro-2,5,7,8-tetramethyl-2-(4,8,12-trimethyl-3,7,11-tridecatrienyl)-2H-1-benzopyran-6-ol; 2,5,7,8-tetramethyl-2-(4,8,12-trimethyl-3,7,11-tridecatrienyl)-6-chromanol; 5,7,8-trimethyltocotrien-3',7',11'-ol;

$zeta_2$-tocopherol, 3,4-dihydro-2,5,7-trimethyl-2-(4,8,12-trimethyltridecyl)-2H-1-benzopyran-6-ol; 2,5,7-trimethyl-2-(4,8,12-trimethyltridecyl-6-chromanol; 5,7-dimethyltocol; and eta-tocopherol, 3,4-dihydro-2,7-dimethyl-2-(4,8,12-trimethyltridecyl)-2H-1-benzopyran-6-ol; 2,7-dimethyl-2-(4,8,12-trimethyltridecyl)-6-chromanol; 7-methyltocol. See *The Merck Index* (1996), Twelfth Edition, Merck & Co., Whitehouse Station, N.J., pp. 1620–1621 and 1712, and references cited therein.

Other tocopherols include $xi_1$-, $xi_2$-, and sigma-tocopherols.

Prototypical tocopherols include alpha-, beta-, gamma- and delta-tocopherol. However, as is known in the art, tocopherols and their derivatives can vary by the number and position of alkyl groups, double bonds and other substituents and variations on the ring and side chain. An "alkyl" is a cyclic, branched or straight chain chemical group containing only carbon and hydrogen, such as methyl, butyl and octyl. Alkyl groups can be either unsubstituted or substituted with one or more substituents, e.g., halogen, alkoxy, acyloxy, amino, hydroxyl, mercapto, carboxy, or benzyl. Alkyl groups can be saturated or unsaturated at one or several positions. Typically alkyl groups will comprise 1 to 8 carbons, preferably 1 to 6, and more preferably 1 to 4 carbon atoms. Additional tocopherols can be constructed by conjugation to the ring structure or side chain of various other moieties, such as those containing oxygen, nitrogen, sulfur and/or phosphorus. Tocopherol derivatives can also be made, as known in the art, by modifying the length of the side chain from that found in prototypical tocopherols such as alpha-, beta-, delta- and gamma-tocopherol. Tocopherols can also vary in stereochemistry and saturation of bonds in the ring structure and side chain. Additional tocopherol derivatives, including prodrugs, can be made by conjugation of sugars or other moieties to the side chain or ring structure; these can serve any of a number of functions, including increasing solubility and increasing functional activity of the tocopherol. Thus, as is understood in the art, the invention encompasses the use of tocopherol derivatives in which substitutions, additions and other alterations have been made in the 6-chromanol ring and/or side chain, with the proviso that the derivatives maintain at least one functional activity of a tocopherol, such as antioxidant activity or ability to counteract sterility in animals. A "tocopherol" for use in the present invention can alternatively be a mixture of tocopherols. These mixtures include without limitation mixtures of stereoisomers of a single tocopherol (e.g., + and − stereoisomers of alpha-tocopherol; (+/−) indicates a racemic mixture) or mixtures of structurally distinct tocopherols (e.g., alpha- plus gamma-tocopherol).

Derivatives of these compounds. include, but are not limited to, salts, including but not limited to succinate, nicotinate, allophanate, acetate, and phosphate salts of the tocopherols described herein. Salts also include pharmaceutically acceptable salts. Derivatives include halogenated derivatives. Derivatives also include quinone derivatives and prodrug forms of tocopherols, such as those described in U.S. Pat. No. 5,114,957. Additional tocopherols and derivatives thereof are described in, e.g., U.S. Pat. No. 5,606,080 and 5,235,073. Preparation of various tocopherols are described in, e.g., U.S. Pat. Nos. 5,504,220, 4,978,617, and 4,977,282. Various tocopherols are available from Sigma Chemical Co., St. Louis, Mo.

By a "non-tocopherol" is meant any compound which is not a tocopherol, tocotrienol, or derivative thereof, or the like.

A "synergist" is defined as an agent which when present results in a greater-than-additive increase, augmentation or enhancement of the cytoprotective effect of a cytoprotective agent. In some cases, it may be difficult to determine which compound in a mixture is of primary importance and which only secondary. Thus, in a synergistic mixture of compounds, any of the active compounds within the mixture can be considered a synergist. A composition comprising "synergistic activity" or a "synergistic mixture" is a combination of compounds which exhibits increased cytoprotective activity as a non-linear multiple of the cytoprotective activity of the individual compounds. In other words, the combined cytoprotective effect of two or more compounds being tested is significantly greater than the expected result based on independent effects of the compounds when tested separately. A "synergistic mixture" is a combination of compounds which exhibits increased cytoprotective activity as a non-linear multiple of the cytoprotective activity of the individual compounds. In other words, the combined cytoprotective effect of two or more compounds being tested is significantly greater than the expected result based on independent effects of the compounds when tested separately. For example, a synergistic mixture can comprise two or more isomers of tocopherol, or a tocopherol and a non-tocopherol such as hesperetin, diosmin or lactoferrin. Synergism may be apparent only at some ranges or concentrations.

An "anti-synergist" is a compound which when present results in a decrease in the cytoprotective potency of a cytoprotective agent. While a combination of compounds at a moderate level can be cytoprotective, higher concentrations can lead to decreased efficacy, e.g., due to increased toxicity of the compounds. Thus, both synergism and anti-synergism may be functions of concentrations and ratios of compounds.

By "optimized formulation" is meant the combination of a tocopherol and an additional compound in amounts determined or predicted to be particularly effective to ameliorate the disruption of energy metabolism secondary to stress. In optimized formulations, the combined amounts of tocopherol and the additional compound are selected to increase, augmentation or enhancement of the cytoprotective effect of either agent when used individually at the same concentration.

By "additional compound" is meant a compound(s) added to another. In a non-limiting example, in a composition comprising a tocopherol and an additional compound, the additional compound is preferably, for example, a non-tocopherol. This can include, as a non-limiting example, a flavonoid, such as daidzein or biochanin A.

By "combination" or "combination of compounds" is meant a selected mixture of compounds.

By "flavonoid" is meant any of a class of polyphenolic molecules based on a flavan nucleus, comprising 15 carbon atoms, arranged in three rings as $C_6$–$C_3$–$C_6$. Flavonoids are generally classified into subclasses by the state of oxidation and the substitution pattern at the C2–C3 unit. As used herein, the term"flavonoid" encompasses, but are not limited to, flavanones, flavonols, flavones, anthocyanidins, chalcones, dihydrochalcones, aurones, flavanols, dihydroflavanols, proanthocyanidins (flavan-3,4-diols), isoflavones and neoflavones. Flavonoids also includes the molecule hesperetin.

As used herein, the term"flavonoids" encompasses, but is not limited to:

diosmin;

hesperidin, (S)-7-[[6-O-(6-Deoxy-α-L-mannopyranosyl)-β-D-glucopyranosyl]oxy]-2,3-dihydro-5-hydroxy-2-(3-hydroxy-4-methoxyphenyl)-4H-1-benzopyran-4-one; hesperetin 7-rhamnoglucoside; cirantin; hesperetin-7-rutinoside;

hesperetin;

rutin, 3-[[6-O-(6-Deoxy-α-L-mannopyranosyl)-β-D-glucopyranosyl]oxy]-2-(3,4-dihydroxyphenyl)-5,7-dihydroxy-4H-1-benzopyran-4-one; rutoside; quercetin-3-rutinoside; 3,3',4',5,7-pentahydroxyflavone-3-rutinoside; melin; phytomelin;

eldrin; ilixathin; sophorin; globularicitrin; paliuroside; osyritrin; osyritin; myrticolorin; violaquercitrin; Birutan; Rutabion; Rutozyd; Tanrutin;

see *The Merck Index* (1989), Eleventh Edition, Merck & Co., Whitehouse Station, N.J., pp. 520, 738, 1319 and references cited therein.

By "diosmin" is meant 7-[[6-O-6-Deoxy-α-L-mannopyranosyl)-β-D-glucopyranosyl]oxy]-5-hydroxy-2-(3-hydroxy-4-methoxyphenyl)-4H-1-benzopyran-4-one; 3',5,7-trihydroxy-4'-methoxyflavone-7-rutinoside; 5-hydroxy-2-(3-hydroxy-4-methoxyphenyl)-7-($O^6$-α-L-rhamnopyranosyl-β-D-glucopyranosyloxy)chromen-4-one; 5-hydroxy-2-(3-hydroxy-4-methoxyphenyl)-7-β-rutinosyloxy-4H-chromen-4-one; diosmetin 7-β-rutinoside; diosmine; barosmin; buchu resin; Daflon; Diosmil; Diovenor; Flebopex; Flebosmil; Flebosten; Flebotropin; Hemerven; Insuven; Tovene; Varinon; Ven-Detrex; Venex; Veno-V; or Venosmine. Derivatives of diosmin are described in, for example, U.S. Pat. Nos. 5,296,469; and 4,894,449. Diosmin is a flavonoid extract; isolation of diosmin from various plant sources is described in, for example, Oesterle et al. (1925) *Helv. Chim. Acta* 8:519; and Horowitz (1956) *J. Org. Chem.* 21:1184; Arthur et al. (1956) *J. Chem. Soc.* 632.

By "hesperetin" is meant the compound (S)-2,3-dihydro-5,7-dihydroxy-2-(3-hydroxy-4-methoxyphenyl)-4H-1benzopyran-4-one; 3',5,7-trihydroxy-4'-methoxyflavanone; cyanidanon 4'-methyl ether 1626. See *The Merck Index* (1996), Twelfth Edition, Merck & Co., Whitehouse Station, N.J., p. 798 and references cited therein. Hesperetin can be prepared by extraction from the peel of citrus fruit or by synthesis. Shinoda et al. (1929) *C.A.* 23:2957; Seka et al. (1936) *Monatsh.* 69:284. The separation of isomers of hesperetin is described in Arthur et al. (1956) *J. Chem. Soc.* 632. The structure and configuration of hesperetin are described in Arakawa et al. (1960) *Ann.* 636:111.

By "lactoferrin" is meant a transferrin found in the milk of several mammalian species and thought to be involved in the transport of iron to erythrocytes. It is approximately 700 amino acids long and is present in relatively high concentrations in human milk. Lactoferrin is the major iron-binding glycoprotein found in milk and other secretions and body fluids, including saliva, tears and mucosal secretions. Lactoferrin comprises two domains, each containing one iron-binding site and one N-linked glycosylation site. These domains show homology to each other, indicative of an ancestral gene duplication and fusion event. In addition, lactoferrin shares extensive sequence identity with other members of the transferrin family. Metz-Boutigue et al. (1984) *Eur. J Biochem.* 1451:659–676; Pentecost et al. (1987) *J. Biol. Chem.* 262:10134–10139. Location of the amino acids involved in iron-binding sites has been determined by X-ray crystallography. Anderson et al. (1987) *Proc. Natl. Acad. Sci. USA* 84:1769–1773. The structure of iron-saturated and iron-free forms of human lactoferrin have been published. Anderson et al. (1989) *J. Mol. Biol.* 209:711–734; Anderson et al. (1990) *Nature* 784–787. Lactoferrin has several other activities, including enhancement of hydroxyl radical production of human neutrophils, enhancement of intestinal iron absorption in infants, promotion of cell growth, and regulation of myelopoiesis and modulation of inflammatory responses. Ambruso et al. (1981) *J. Clin. Invest.* 67:352–360. Lactoferrin also has antibacterial and antifungal activities. Arnold et al. (1977) *Science* 197:263–265; Soukka et al. (1992) *FEMS Microbiol. Lett.* 90:223–228. Lactoferrin and some of its derivatives are reviewed in, for example, Levay et al. (1995) *Haematologica* 80:252–267; Britigan et al. (1994) *Adv. Exp. Med. Biol.* 357:143–156; Tomita et al. (1994) *Acta Paediatr. Jpn.* 36:585–591; Sanchez et al. (1992) *Arch. Dis. Child.* 67:657–661; Tomita et al. (1994) *Acta Paediat. Japon.* 36:585–591; Levay et al. (1995) *Haematologica* 80:252–267; *Advances in Lactoferrin Research,* ed. Spik et al., Plenum Press, New York; Lonnerdal et al. (1995) *Ann. Rev. Nutr.* 15:93–110; Sanchez et al. (1992) *Archiv. Disease Childhood* 67:657–661; and Fleet et al. (1995) *Nutrition Rev.* 53:226–231.

By "daidzein" is meant 7-hydroxy-3-(4-hydroxyphenyl)-4H-1-benzopyran-4-one; or 4',7-dihydroxyisoflavone. See *The Merck Index* (1996), Twelfth Edition, Merck & Co., Whitehouse Station, N.J., p. 475 and references cited therein. Isolation of daidzein from various plant products is described in Hosny et al. (1999) *J. Nat. Prod.* 62: 853–8; Walz (1931) *Ann.* 489:118; and Wong (1962) *J. Sci. Food Agr.* 13:304. Synthesis is described in Farkas et al. (1959) *Ber.* 92:819. Daidzein is an inactive analog of the tyrosine kinase inhibitor genistein. Sargeant et al. (1993) *J. Biol. Chem.* 268:18151. Daidzein is also a phytoestrogen, recently suggested to play a role in preventing special types of cancer. Sathyamoorthy et al. (1994) *Cancer Res.* 54:957; Zhou et al. (1999) *J. Nutr.* 129: 1628–35; and Coward et al. (1993) *J. Agric. Food Chem.* 41: 1961. Daidzein also has anti-estrogen properties. Anderson et al. (1998) *Baillieres Clin. Endocrinol. Metab.* 12: 543–57. Daidzein also acts as an anti-oxidant, inhibiting lipid peroxidation. Arora et al. (1998) *Arch. Biochem. Biophys.* 356: 133–41; and Hodgson et al. (1999) *Atherosclerosis* 145: 167–72. Daidzein is also useful for treating Alzheimer's disease. U.S. Pat. Nos. 5,952,374; and 5,733,926. Daidzein also alters the concentration of cholesterol constituents in human blood. U.S. Pat. No. 5,855,892.

By "biochanin" or "biochanin A" is meant 5,7-dihydroxy-4'-methoxyiso-flavone; or olmelin. See *The Merck Index* (1996), Twelfth Edition, Merck & Co., Whitehouse Station, N.J., p. 744 and references cited therein. Biochanin A can be isolated from red clover. Pope et al. (1953) *Chem. & Ind.* (London) 1092; and Wong (1962) *J. Sci. Food. Agr.* 13:304. Its structure is described by Bose et al. (1950) *J. Sci. Ind. Res.* 9B: 25. Biochanin A also has some anti-cancer properties. Lyn-Cook et al. (1999) *Cancer Lett.* 142: 111–9; Hammons et al. (1999) *Nutr. Cancer* 33: 46–52; Yin et al. (1999) *Thyroid* 9: 369–76. Biochanin A also has anti-oxidant properties, including the ability to inhibit lipid peroxidation. Toda et al. (1999) *Phytother. Res.* 13: 163–5.

By "derivative" is meant a compound derived from and thus non-identical to another compound. As used herein, a derivative shares at least one function with the compound from which it is derived, but differs from that compound structurally.

Derivatives of tocopherols include without limitation those that differ from tocopherols due to modifications (including without limitation substitutions, additions and deletions) in the ring structure or side chain. Derivatives of lactoferrin include those which differ from lactoferrin in length and/or amino-acid sequence (e.g., by substitution, rearrangement, deletion, or addition in sequence), or in post-translational modification (e.g., methylation, iron association, glycosylation, or lack thereof).

Derivatives of hesperetin include those compounds which differ from hesperetin in structure. These structural differences can be,.as non-limiting examples, by addition, substitution or re-arrangement of hydroxyl, alkyl or other group. As a non-limiting example, a hesperetin derivative can have additional (substituted or non-substituted) alkyl groups attached. In addition, hesperetin derivatives include compounds which have been conjugated to another chemical moiety, such as a sugar or other carbohydrate. Derivatives also include salts of tocopherols, lactoferrin and hesperetin. Derivatives of daidzein, biochanin A and other compounds described herein include compounds which are chemically and/or structurally similar, but non-identical to such compounds, and which share at least one function of those compounds. Numerous derivatives of daidzein are known in the art. These include daidzein 7-glucoside, or daidzin; and the aglucon of daidzein. Glycosylated and methoxylated derivatives of daidzein are described in Arora et al. (1998). Chlorinated derivatives of daidzein are described in Boersma et al. (1999) *Arch. Biochem. Biophys.* 368: 265–75. Additional derivatives are described in Lapcik et al. (1997) *Steroids* 62: 315–20; Joannou et al. (1995) *J. Steroid. Biochem. Mol. Biol* 54: 167–84; Keung (1993) *Alcohol Clin. Exp. Res.* 17: 1254–60; Smitet al. (1992) *J. Biol. Chem.* 267: 310–8; Shao et al. (1980) *Yao Hsueh Hsueh Pao* 15: 538–47; and King et al. (1998) *Am. J Clin. Nutr.* 68: 1496S–1499S. Numerous derivatives of biochanin A are also described in the art, in, for example, chlorinated derivatives described in Boersma et al. (1999).

An "equivalent derivative" is a derivative that when present results in a greater-than-additive increase, augmentation or enhancement of a cytoprotective agent, and preferably of at least the same order of magnitude as the synergist from which it is derived.

By a "amounts effective to ameliorate injury(ies) or disruption of energy metabolism" is meant that the cytoprotective agent or agents (e.g., tocopherol or mixture comprising a tocopherol) is present in a final concentration sufficient for amelioration of injury(ies) or disruption of energy metabolism. This amount includes, but is not limited to, a concentration which acts as a complete prophylaxis or treatment for a symptom of stress. An "effective amount" is an amount sufficient to effect beneficial or desired results. An effective amount can be administered in one or more administrations. For purposes of this invention, an effective amount of a cytoprotective composition is an amount that is sufficient to ameliorate, stabilize, reverse, slow or delay the progression of the injury(ies) or disruption of energy metabolism. Preferably, amelioration of injury(ies) or disruption of energy metabolism can be quantified by an assay measuring, for example, cell death or enzyme inactivity. Amelioration is preferably at least about 30%, preferably at least about 50%, more preferably at least about 70%, even more preferably at least about 80%, and even more preferably at least about 90%.

"Alteration" or "disruption" of "energy metabolism" refers to a disturbance in normal oxidative metabolism or respiration. Such alteration can be measured by decreases or increases in levels of ATP, decreases in energy charge and/or imbalances in redox pairs which disrupt the normal function and/or homeostasis of cells, tissues, organs and/or organisms. Alterations can be detectable as, for example, changes in membrane integrity, membrane potential, electron transport flux, mitochondrial membrane potential, substrate utilization, release of intracellular components, altered cell or tissue function (e.g., changes in muscle tissue activity), release of lactate, cytosolic ROS, ATP levels, adenosine and purine metabolism, and energy charge and redox charge. These alterations can be induced experimentally by chemical interference (e.g., by using toxins such as antimycin or iodoacetate) or by changing the environmental conditions in the laboratory (e.g., by inducing anoxia, hypothermia, hyperthermia, etc.).

The term "energetically-competent" or "oxidatively competent" refers to cells, cell lines or organisms which undergo aerobic respiration (oxidative metabolism). "Energetically incompetence" refers to the quality of cells incapable of undergoing aerobic respiration; such cells only perform anaerobic respiration (fermentation).

By "stress" is meant any disturbance in normal homeostasis or well-being of a living biological entity or subject. A stress is any condition wherein a cell, organ or organism undergoes damage, and encompasses any condition which can affect an entity's ability to survive, procreate or carry out normal life functions. By "stresses secondary to alteration, inhibition or disruption of energy metabolism" is meant those injury(ies) to cells, organs or organisms associated with, resulting in or caused by alterations in oxidative metabolism or respiration. These include, but are not limited to, environmental, chemical and physiological stresses. Environmental stresses include, but are not limited to, hypothermia, hyperthermia, hypoxia, and ionizing radiation. Chemical stresses include, but are not limited to, drug toxicity, chemotherapy, toxins, and artificial environments (i.e., cell culture). Physiological stresses include, but are not limited to, injuries concomitant with disease prevention, disease recovery, health maintenance, physical exertion, aging, and pre-surgical and post-surgical situations. The results of stress can have detectable manifestations, including, but not limited to, induction of cell death, increased cell membrane permeability, excessive production of free radicals, and decreased metabolism and enzyme activity.

Stresses also include, but are not limited to, conditions listed below:

"Hypothermia" which is broadly defined as a condition of abnormally low body temperature. Normal body temperatures for various species are known in the art. For example, a the normal core body temperature for a human being is about 37° C. For humans, hypothermia can be clinically measured as a condition of the core body temperature of 35° C. or less. Accidental hypothermia occurs when heat loss to the environment exceeds the body's ability to produce heat internally.

"Hyperthermia" is a condition of abnormally high body temperature (above 37° C.). For humans, hyperthermia is sometimes defined more specifically as a condition of having a core body temperature of between about 38.5° C. and 41.5° C.

"Hypoxia" which is defined broadly as a condition under which a particular cell, organ or tissue receives an insufficient oxygen supply to allow normal function. More specifically, hypoxia can be measured as an average or mean environmental oxygen saturation level of less than 90%.

"Ionizing radiation" which refers to radiation consisting of streams of subatomic particles, such as protons, neutrons and electrons, or radiation originating in a varying electromagnetic field, e.g., long and short radio waves, light (visible and invisible), x-irradiation and gamma rays that is of sufficient energy to ionize the irradiated material. The term "to ionize" means to dissociate atoms or molecules into electrically charged atoms or radicals.

"Chemical insult" which refers to an injury or trauma that results from contact with a chemical substance. A chemical insult can refer to an injury to a cell, an organ and/or an individual.

"Drug toxicity" which refers to the state of being poisoned or injured due to the presence of and/or contact with a drug. The amount of toxicity associated with a drug may vary with several conditions including, but not limited to, the amount of drug present, the formulation of the drug and the environmental conditions of the affected cell, organ and/or individual.

"Chemotherapy" which refers to a treatment of a disease by means of chemical substances or drugs, typically cytotoxic drugs. Chemotherapeutic regimens are well-known in the art to result in a number of side effects.

"Toxin" which is a substance that is noxious or poisonous to a cell and/or organism.

"Physical exertion" which refers to bodily action in excess of resting state that can result in tiredness or fatigue, or depletion of biological energy stores (e.g., glucose or glycogen).

"Aging" which refers to the gradual deterioration of a cell, organ and/or individual resulting from time-dependent, irreversible changes in structure and/or function of the particular cell, organ and/or individual.

"Pre-surgical preparation" by which is meant treatments administered to a cell, organ and/or individual prior to a surgical manipulation. Pre-surgical preparations include, but are not limited to, treatments of tissues, organs and/or cells prior to transplantation.

"Post-surgical" conditions, which term refers to the state or condition of a cell, organ and/or individual after a surgical procedure. Post-surgical conditions include, but are not limited to, reperfusion of tissues, organs and/or cells.

A "subject" is a cell, an organ, a whole organism or an individual. An "individual" is a vertebrate, including, but not limited to, avians, reptiles and mammals. Mammals include, but are not limited to, humans, farm animals, sport animals, and pets.

By "amelioration" is meant improvement of the state of a subject; the amelioration of a stress is the counter-acting of the negative aspects of a stress. Amelioration includes, but does not require complete recovery or complete prevention of a stress.

As used herein, the term "comprising" and its cognates are used in their inclusive sense; that is, equivalent to the term "including" and its corresponding cognates.

General Methods

General techniques for chemical manipulations are known in the art and are generally described in, for example, Haugland (1996) *Handbook of Fluorescent Probes and Research Chemicals,* Sixth Edition, Molecular Probes, Inc.; Carruthers (1986) *Some Modern Methods of Organic Synthesis,* Third Edition, Cambridge University Press; and Warren (1978) *Designing Organic Syntheses,* John Wiley & Sons, Ltd. Molecular biology techniques are generally described in, for example, Sambrook et al. (1989), *Molecular Cloning: A Laboratory Manual,* Second Edition; and Ausubel et al., eds. (1987) *Current Protocols In Molecular Biology.* Reagents useful in applying these techniques are widely known in the art and commercially available from a number of vendors.

Compositions

Provided herein are non-naturally-occurring compositions comprising a tocopherol and a synergist or other additional compound, and equivalent derivatives thereof, for use as cytoprotectants against disruption of energy metabolism secondary to stress. These compounds are present in the compositions in amounts effective to ameliorate the injury (ies) or disruption of energy metabolism secondary to stress.

Tocopherols are chemical entities which, in general, contain a 6-chromanol ring structure and a side chain at the 2-position. Prototypical tocopherols include alpha-, beta-, gamma- and delta-tocopherol. However, as is known in the art, tocopherols and their derivatives can vary by the number and position of alkyl groups, double bonds and other substituents and variations on the ring and side chain. An "alkyl" is a cyclic, branched or straight chain chemical group containing only carbon and hydrogen, such as methyl, butyl and octyl. Alkyl groups can be either unsubstituted or substituted with one or more substituents, e.g., halogen, alkoxy, acyloxy, amino, hydroxyl, mercapto, carboxy, or benzyl. Alkyl groups can be saturated or unsaturated at one or several positions. Typically alkyl groups will comprise 1 to 8 carbons, preferably 1 to 6, and more preferably 1 to 4 carbon atoms. Additional tocopherols can be constructed by conjugation to the ring structure or side chain of various other moieties, such as those containing oxygen, nitrogen, sulfur and/or phosphorus. Tocopherol derivatives can also be made, as known in the art, by modifying the length of the side chain from that found in prototypical tocopherols such as alpha-, beta-, delta- and gamma-tocopherol. Tocopherols can also vary in stereochemistry and saturation of bonds in the ring structure and side chain. Additional tocopherol derivatives, including prodrugs, can be made by conjugation of sugars or other moieties to the side chain or ring structure; these can serve any of a number of functions, including increasing solubility and increasing functional activity of the tocopherol. Thus, as is understood in the art, the invention encompasses the use of tocopherol derivatives in which substitutions, additions and other alterations have been made in the 6-chromanol ring and/or side chain, with the proviso that the derivatives maintain at least one functional activity of a tocopherol, such as antioxidant activity or ability to counteract sterility in animals. A "tocopherol" for use in the present invention can alternatively be a mixture of tocopherols. These mixtures include without limitation mixtures of stereoisomers of a single tocopherol (e.g., +and − stereoisomers of alpha-tocopherol) or mixtures of structurally distinct tocopherols (e.g., alpha- plus gamma-tocopherol). Mixtures of tocopherols can have higher activity than single tocopherols, as demonstrated in Example 6. Thus, the composition of the present invention can comprise two or more tocopherols and a synergist or additional compound.

Activity of a tocopherol or tocopherol derivative (alone or in combination with a synergist or additional compound) can also be experimentally tested, for example, in an assay which measures ability to ameliorate injury(ies) or disruption of energy metabolism secondary to stress. Such assays (which are detailed in Examples 1 to 4) include without limitation the use of energetically competent cell and cell lines, wherein energy metabolism is experimentally disrupted (e.g., by addition of a toxin or altering the temperature or oxygen level). Tocopherols and derivatives suitable for the present invention include those which are (alone or in combination with a synergist or additional compound) capable of ameliorating injury(ies) or disruption of energy metabolism secondary to stress, as indicated, for example, by a reduction in membrane permeability, excessive production of free radicals, inhibition of enzyme activity, or induction of cell death secondary to alteration in energy metabolism. Amelioration of the injury(ies) or disruption of energy metabolism secondary to stress can be measured by various means, including without limitation fluorescent measurements. Preferably, reduction in the injury(ies) or disruption of energy metabolism secondary to stress is quantified at least about 30%, preferably at at least about 50%, more preferably at at least about 70%, even more preferably at at least about 80%, and even more preferably at at least about 90%.

The invention relates to the use of a combination of a tocopherol and a synergist or additional compound, wherein the combinations are suitable for ameliorating a disruption of energy metabolism secondary to stress.

By way of example, an exemplary nutritional formulation composition or dosing regimen might include the following components in a daily or divided daily dose: alpha tocopherol or a mixture of alpha and gamma tocopherol ranging from about 10–1000 mg, preferably about 50–600 mg, hesperitin, ranging from about 10–500 mg, preferably about 25–200 mg in a divided daily dose, and quercetin, ranging from about 10–500 mg, preferably about 50–300 mg in a divided daily dose. By way of specific example, taking into consideration doses that are considered safe for human consumption, a beneficial nutritional supplement in accordance with the present invention might include, for example, 200–500 mg alpha tocopherol, once daily, 100–300 mg each quercetin and hesperetin divided between two to three daily doses. In this specific regimen, gamma tocopherol could replace in whole or part the alpha tocopherol component; while another flavonoid or flavonoids could replace one or both of the flavonoids indicated. Such a specific dosing regimen forms part of the invention.

In certain embodiments, the synergist can be a lactoferrin or lactoferrin derivative. Lactoferrin is the major iron-binding glycoprotein found in milk and other secretions and body fluids, including saliva, tears and mucosal secretions. Suitable lactoferrins include those derived from various mammals including humans, and derivatives thereof. Lactoferrin sequences known in the art include without limitation those which are human [Metz-Boutigue et al. (1984) *Eur. J. Biochem.* 1451:659–676; Rado et al. (1987) *Blood* 70:989–993; Rey et al. (1990) *Nucl. Acids Res.* 18:5288; Powell et al. (1990) *Nucl. Acids Res.* 18:4013; U.S. Pat. No. 5,741,957], bovine [Mead et al. (1990) *Nucl. Acids Res.* 18:7167; Goodman et al. (1991) *Biochem. Biophys. Res. Comm.* 180:75–84; Pierce et al. (1991) *Eur. J. Biochem.* 196:177–184; U.S. Pat. No. 5,741,957], porcine [Pentecost et al. (1987) *Biochim. Biophys. Acta* 1132:97–99; Lydon et al. (1992) *Biochim. Biophys. Acta* 1132:97–99; Alexander et al. (1992) *Animal Genetics* 23:251–256], equine [Shimazaki et al. (1994) *J. Dairy Res.* 61:563–6; and Hutchens et al. (1989) *Biochim. Biophys. Acta* 999:323–9] and murine [Cunningham et al. (1992) *Biochem. Biophys. Res. Comm.* 189:1725–1731; and Shirsat et al. (1992) *Gene* 110: 229–234] lactoferrins. Preferably, the lactoferrin used as a synergist is human.

Also suitable for use in the present invention are derivatives of lactoferrin which differ from any of the known lactoferrin sequences by sequence differences, including substitution, deletion, addition, or insertion of amino acids. Sequence determination can be performed by any method known in the art, including, for example, that described in Sanger et al. (1977) *Proc. Natl Acad. Sci. U.S.A.* 74:5463–5467 or use of Sequenase™ kit (U. S. Biochemical Corp., Cleveland, Ohio). Preferably, the lactoferrin derivative has at least about 60% (amino acid) sequence identity, more preferably at least about 70%, even more preferably at least about 80% identity, and most preferably at least about 90% sequence identity with the amino acid sequence of a known lactoferrin sequence. Sequences for comparison are optimally aligned (gapped, if necessary) to calculate sequence identity. If the lactoferrin derivative differs in length from any known lactoferrin, sequence identity is calculated based on the shorter sequence. Sequence identity can be measured by sequence analysis software known in the art; a preferred software package is the Sequence Analysis Software Package of the Genetics Computer Group, University of Madison-Wisconsin. See, for example, Devereaux et al. (1984) *Nucl. Acids. Res.* 12:387–395. Additional methods for determining sequence identity are provided in: Griffin et al., eds. (1994), *Computer Analysis of Sequence Data, Part I*, Humana Press, New Jersey; von Heinje (1987), *Sequence Analysis in Molecular Biology*, Academic Press; Gribskov et al., eds. (1991), *Sequence Analysis Primer*, M Stockton Press, New York; and Carillo et al. (1988) *SIAM J. Applied Math.* 48: 1073. Suitable lactoferrins and derivatives which differ from known lactoferrins include allelic variants. Suitable lactoferrins which differ from known lactoferrins in sequence also mediate at least one known activity of a lactoferrin, such as iron storage and/or transport, antibacterial or antifungal activity, DNA binding and transcription activity, or modulation of immune function. These various activities are described in detail in the lactoferrin reviews cited herein.

Lactoferrins suitable for the present invention also include fragmentary derivatives of full-length lactoferrin, which is about 78 kDa in size. Lactoferrins comprise two domains or lobes (amino acids 1 to 338 and 339 to 703), each containing an iron-binding site and a N-linked glycosylation site. Each lobe can reversibly bind one ferric iron with high affinity and with the concomitant binding of bicarbonate. Lactoferrin also comprises a 52-amino-acid-long N-terminal bacteriocidal domain [Bellamy et al. (1992) *Biochim. Biophys. Acta* 1121:130–136]. See also, Montreuil et al. (1985) *Proteins of Iron Storage and Transport*, Spik et al. (eds.), pp. 25–38. The location of the amino acids involved in iron-binding sites has been determined by X-ray crystallography [Anderson et al. (1987) *Proc. Natl. Acad. Sci. USA* 84:1769–1773]. Fragments of lactoferrin which retain at least one lactoferrin activity have been described in the art. Rado et al. (1987). Iron-binding fragments from the N- and C-terminal regions of lactoferrin have also been described in Bluard-Deconinck et al. (1978) *Biochem. J.* 171:321–327. An iron-binding, 18-kDa glycopeptide from the N-terminus of lactoferrin was described in LeGrand et al. (1984) *Biochim. Biophys. Acta.* 787:90–96. An 18-amino acid cleavage product of lactoferrin also shows independent biological activity. Tomita et al. (1994). Suitable derivatives retain at least one activity typical of lactoferrin, comprise at least a portion of at least one domain of a lactoferrin, and within that portion have at least about 60%, preferably at least about 70%, more preferably at least about 80%, and most preferably at least about 90% sequence identity with the amino acid sequence of a known lactoferrin. Preferably, the lactoferrin fragment comprises at least about 15, at least about 20, at least about 30, at least about 40, at least about 50, at least about 100, at least about 200, at least about 200, at least about 300, at least about 400, at least about 500, or at least about 600 amino acids of the lactoferrin sequence.

In addition, lactoferrins suitable for the present invention include fusion proteins comprising (1) a full-length (e.g., approximately 700-amino-acid long) lactoferrin or a derivative thereof, and (2) at least one fusion partner, which is a domain, protein or polypeptide which is not a lactoferrin or derivative thereof. This fusion partner can be a fully-functional protein or active derivative thereof (e.g., a secretory signal protein or sequence, a serum protein, a glycoprotein, etc.). Alternately, the fusion partner can be an amino acid or short polypeptide; e.g., a methionine, or a short polypeptide useful for increasing the solubility, production or stability of the fusion protein (such as a hexahistidine, STII signal peptide, or FLAG polypeptide, as known in the art). The fusion protein can comprise multiple non-lactoferrin amino-acid sequences (e.g., a methionine, a FLAG and a serum protein sequence). Preferably, fusion proteins suitable for the invention comprise at least one active lactoferrin domain and a non-lactoferrin sequence. Lactoferrins and derivatives suitable for the present invention also include those which are chimeras (fusions) containing domains or lobes from different species. For example, a lactoferrin or derivative can comprise one domain from one species and another domain from another. Furthermore, the various lactoferrin domains need not be in the order in which they are present in naturally-occurring lactoferrins or, indeed, need not be physically connected, provided that at least one lactoferrin activity is retained by the lactoferrin or lactoferrin derivative.

Lactoferrins and derivatives suitable for the present invention can also be post-translationally modified, including phosphorylation, methylation, glycosylation, and conjugation to other chemical moieties. Lactoferrins and derivatives can also be iron-free or iron-saturated. Post-translational modifications of lactoferrin are described in the art, e.g., in Panella et al. (1991) *Cancer Res.* 51:3037–3043; and Anderson et al. (1987) and (1989).

Lactoferrins and derivatives suitable for the present invention can be recombinantly or naturally produced. Ward et al. (1997) *Biotech. Genet. Engin. Rev.* 14:303–319. Methods for recombinant production of lactoferrin, e.g., using lactoferrin cDNA sequences, are described in U.S. Pat. Nos. 5,766,939; and 5,849,881; and Ward et al. (1992) *Biotech.* 10:784–789; Stowell et al. (1991) *Biochem. J.* 276:349–355. Methods for purification of lactoferrin from natural sources, e.g., purification of human and bovine lactoferrin from milk, are described in, for example, U.S. Pat. Nos. 5,919,913; 5,849,885; and 5,861,491.

Lactoferrins and derivatives thereof suitable for use as synergists in the present invention include those which are, in combination with a tocopherol, capable of ameliorating stress, as indicated, for example, by a reduction in membrane permeability, excessive production of free radicals, inhibition of enzyme activity, or induction of cell death secondary to alteration in energy metabolism. Amelioration of stress can be measured by various means, including without limitation fluorescent measurements. Preferably, reduction in stress is quantified at at least about 30%, preferably at at least about 50%, more preferably at at least about 70%, even more preferably at at least about 80%, and even more preferably at at least about 90%.

The invention relates to the use of a combination of a tocopherol and a synergist or additional compound, wherein the combinations are suitable for ameliorating a disruption of energy metabolism secondary to stress. While exemplary synergistic combinations are exemplified herein, it is appreciated that specific molar combination ratios may be determined empirically, in accordance with the teachings provided herein.

In certain embodiments, the synergist can be a flavonoid, such as hesperetin or a hesperetin derivative. Flavonoids are phenylbenzo-γ-pyrones and are a class of polyphenolic substances based on a flavan nucleus, comprising 15 carbon atoms, arranged in three rings as $C_6$–$C_3$–$C_6$. There are a number of chemical variations of the flavonoids, such as, the state of oxidation of the bond between the C2–C3 position and the degree of hydroxylation, methoxylation. or glycosylation (or other substituent moieties) in the A, B and C rings and the presence or absence of a carbonyl at position 4. Flavonoids include, but are not limited to, members of the following subclasses: chalcone, dihydrochalcone, flavanone, flavonol, dihydroflavonol, flavone, flavanol, isoflavone, neoflavone, aurone, anthocyanidin, proanthocyanidin (flavan-3,4-diol) and isoflavane.

Flavanones contain an asymmetric carbon atom at the 2-position and flavanones include, but are not limited to, narigenin, naringin, eriodictyol, hesperetin and hesperidin. Dihydroflavonols include, but are not limited to, taxifolin (dihydroquercetin). Flavones include, but are not limited to, chrysin, diosmin, luetolin, apigenin, tangeritin and nobiletin. Flavonols include, but are not limited to, kampferol, quercetin and rutin. Flavanes include, but are not limited to, catechin and epi-gallocatechin-gallate. Isoflavones include, but are not limited to, biochanin, daidzein, glycitein and genistein.

As used herein, the term "flavonoids" encompasses, but is not limited to:

chrysin, 5,7-dihydroxy-2-phenyl-4H-1-benzopyran-4-one; 5,7-dihydroxyflavone; chrysidenon 1438;

daidzein, 7-hydroxy-3-(4-hydroxyphenyl)-4H-1-benzopyran-4-one; 4',7-dihydroxyisoflavone;

diosmin, 7-[[6-O-6-Deoxy-α-L-mannopyranosyl)-β-D-glucopyranosyl]oxy]-5-hydroxy-2-(3-hydroxy-4-methoxyphenyl)-4H-1-benzopyran-4-one; 3',5,7-trihydroxy-4'-methoxyflavone-7-rutinoside; 5-hydroxy-2-(3-hydroxy-4-methoxyphenyl)-7-($O^6$-α-L-rhamnopyranosyl-β-D-glucopyranosyloxy)chromen-4-one; 5-hydroxy-2-(3-hydroxy-4-methoxyphenyl)-7-p-rutinosyloxy-4H-chromen-4-one; diosmetin 7-β-rutinoside; barosmin; buchu resin; Daflon; Diosmil; Diovenor; Flebopex; Flebosmil; Flebosten; Flebotropin; Hemerven; Insuven; Tovene; Varinon; Ven-Detrex; Venex; Veno-V; Venosmine;

hesperetin, (S)-2,3-dihydro-5,7-dihydroxy-2-(3-hydroxy-4-methoxyphenyl)-4H-1-benzopyran-4-one; 3',5,7-trihydroxy-4'-methoxyflavanone; cyanidanon 4'-methyl ether 1626;

hesperidin, (S)-7-[[6-O-(6-Deoxy-α-L-mannopyranosyl)-β-D-glucopyranosyl]oxy]-2,3-dihydro-5-hydroxy-2-(3-hydroxy-4-methoxyphenyl)-4H-1-benzopyran-4-one; hesperetin 7-rhamnoglucoside; cirantin; hesperetin-7-rutinoside;

luteolin, 2-(3,4-Dihydroxyphenyl)-5,7-dihydroxy-4H-1-benzopyran-4-one; 3',4',5,7-tetrahydroxyflavone; digitoflavone; cyanidenon 1470;

quercetin, 2-(3,4-Dihydroxyphenyl)-3,5,7-trihydroxy-4H-1-benzopyran-4-one; 3,3',4',5,7-pentahydroxyflavone; memtin; sophoretin; cyanidenolon 1522;

rutin, 3-[[6-O-(6-Deoxy-α-L-mannopyranosyl)-β-D-glucopyranosyl]oxy]-2-(3,4-dihydroxyphenyl)-5,7-dihydroxy-4H-1-benzopyran-4-one; rutoside; quercetin-3-rutinoside; 3,3',4',5,7-pentahydroxyflavone-3-rutinoside; melin; phytomelin; eldrin; ilixathin; sophorin; globularicitrin; paliuroside; osyritrin; osyritin; myrticolorin; violaquercitrin; Birutan; Rutabion; Rutozyd; Tanrutin; see *The Merck Index* (1989), Eleventh Edition, Merck & Co., Whitehouse Station, N.J., pp. 350, 441, 520, 738, 883, 1278, 1319 and references cited therein.

Hesperetin is exemplified herein as one of a class of compounds known as flavonoids, which are polyphenolic molecules based on a flavan nucleus, comprising 15 carbon atoms, arranged in three rings as $C_6$–$C_3$–$C_6$. Flavonoids are generally classified into subclasses by the state of oxidation and the substitution pattern at the C2–C3 unit. As used herein, the term "flavonoid" encompasses, but are not limited to, flavanones, flavonols, flavones, anthocyanidins, chalcones, dihydrochalcones, aurones, flavanols, dihydroflavanols, proanthocyanidins (flavan-3,4-diols), isoflavones and neoflavones. Flavanoids exemplified hereing includes the molecules hesperetin, diosmin, daidzein and biochanin.

Hesperetin acts synergistically with (+/−)-alpha-tocopherol, (+)-alpha-tocopherol Type V, (+)-gamma-tocopherol and (+)-delta-tocopherol.

Hesperetin is the compound (S)-2,3-dihydro-5,7-dihydroxy-2-(3-hydroxy-4-methoxyphenyl)-4H-1-benzopyran-4-one; 3',5,7-trihydroxy-4'-methoxyflavanone; cyanidanon 4'-methyl ether 1626. See *The Merck Index* (1996), Twelfth Edition, Merck & Co., Whitehouse Station, N.J., p. 798 and references cited therein.

Also suitable as synergists in the present invention are derivatives of hesperetin. The derivatives differ from hesperetin in structure. These differences can be, as non-limiting examples, by addition, substitution or re-arrangement of hydroxyl, alkyl or other group. As a non-limiting example, a hesperetin derivative can have additional alkyl groups attached. In addition, hesperetin derivatives include compounds which have been conjugated to another chemical moiety, such as a sugar or other carbohydrate. Other suitable moieties contain oxygen, nitrogen, sulfur, and/or phosphorus. Derivatives of hesperetin can be produced, for example, to improve its solubility, reduce its odor or taste, or to ensure that the compound is free of toxicity. Hesperetin can also be conjugated to another moiety to form a prodrug. In a prodrug, hesperetin is conjugated to a chemical moiety which, for example, aids in delivery of hesperetin to the site of activity (e.g., a particular tissue within the body). This chemical moiety can be optionally cleaved off (e.g., enzymatically) at that site. Hesperetin derivatives are described in, for example, Esaki et al. (1994) *Biosci. BiotechnoL Biochem.* 58:1479–85; Scambia et al. (1990) *Anticancer Drugs* 1:45–8; Bjeldanes et al. (1977) *Science* 197:577–8; Honohan et al. (1976) *J. Agric. Food Chem.* 24:906–11; and Brown et al. (1978) *J. Agric. Food Chem.* 26:1418–22.

While differing from hesperetin in structure, derivatives of hesperetin will retain at least one activity of hesperetin. These activities include anti-oxidant and anti-free radical activity. Saija et al. (1995) *Free Radic. Biol. Med.* 19:481–6. Hesperetin is also an antilipolytic in rat adipocytes. Kuppusamy et al. (1993) *Planta Med.* 59:508–512. Hesperetin also has activity in controlling sebum production and treatment of side disorders. U.S. Pat. No. 5,587,176. Hesperetin may also act in inhibiting mammary tumorigenesis and proliferation of breast cancer cells. Guthrie et al. (1998) *Adv. Exp. Med. Biol.* 439:227–36; So et al. (1997) *Cancer Left.* 112:127–33. Hesperetin also inhibits 7-ethoxycoumarin)-deethylase activity in rat liver microsomes. Moon et al. (1998) *Xenobiotica* 28:117–26. Hesperetin also reduces the susceptibility of membrane $Ca^{2+}$-ATPase to thyroid hormone stimulation. Hesperetin also increases ocular blood flow. Liu et al. (1996) *J. Ocul. Pharm. Ther.* 12:95–101. Hesperetin also inhibits myeloperoxidase. 'T Hart et al. (1990) *Chem. Biol. Interact.* 73:323–35. Hesperetin also inhibits 3-hydroxy-3-methylglutaryl CoA reducatase. U.S. Pat. No. 5,763,414. Hesperetin derivatives retain at least one of these activities.

An alternative synergist suitable for the present invention is diosmin, or a derivative thereof. Diosmin is a flavonoid extract, 7-[[6-O-6-Deoxy-α-L-mannopyranosyl)-β-D-glucopyranosyl]oxy]-5-hydroxy-2-(3-hydroxy-4-methoxyphenyl)-4H-1-benzopyran-4-one. See *The Merck Index* (1996), Twelfth Edition, Merck & Co., Whitehouse Station, N.J., p. 558, and references cited therein.

Also suitable as synergists are derivatives of diosmin. Derivatives of diosmin differ from diosmin in structure. These differences can be, as non-limiting examples, by addition, substitution or re-arrangement of hydroxyl, alkyl or other group. As a non-limiting example, a diosmin derivative can have at least one additional alkyl group added. In addition, diosmin derivatives include compounds which have been conjugated to another chemical moiety, such as a sugar or other carbohydrate. Other suitable moieties contain oxygen, nitrogen, sulfur and/or phosphorus. Diosmin can also be conjugated to another moiety to form a prodrug. Derivatives of diosmin include diosmin heptakis (hydrogensulfate) aluminum complex, and diosmin octakis (hydrogen sulfate) aluminum complex, as described in U.S. Pat. Nos. 5,296,469; and 4,894,449. Another derivative of diosmin is its aglycone form, diosmetin, 5,7-dihydroxy-2-(3-hydroxy-4-methoxypenyl)-4H-1-benzopyran-4-one. See *The Merck Index* (1996), Twelfth Edition, Merck & Co., Whitehouse Station, N.J., p. 558, and references cited therein. Derivatives of diosmin also include salts thereof. A synthetic diosmin derivative, LEW-10, is described in Azize et al. (1992) Chem. Phys. Lipids 63: 169–77.

While differing from diosmin in structure, diosmin derivatives will retain at least one activity of diosmin. Diosmin is commonly administered to protect blood vessels and prevent and/or treat herpesvirus attacks. Diosmin also has free radical scavenger activity [Dumon et al. (1994) *Ann. Biol. Clin.* 52: 265–270]; is an antilipoperoxidant [Feneix-Clerc et al. (1994) *Ann. Biol. Clin.* 52:171–7]; inhibits 5'-nucleotidase [Kavutcu et al. (1999) *Pharmazie* 54:457–9]; attenuates lipopolysaccharide cytotoxicity in cell culture [Melzig et al. (1999) *Pharmazie* 54:29809]; probably affects cytochrome P450 activity [Teel et al. (1998) *Cancer Lett.* 133:135–141; and Ciolino et al. (1998) *Cancer Res.* 58:2754–60]. The combination of diosmin and hesperidin, known as Daflon 500 mg, has anti-inflammatory, anti-free radical, venotonic and vasculoprotective activities, in addition to attenuating reperfussion injury. Guillot et al. (1998) *Pancreas* 17:301–8; Amiel et al. (1998) *Ann. Cardiol. Angeiol.* 47:185–8; Nolte et al. (1997) *Int. J. Microcirc. Clin. Exp.* 17 (suppl. 1): 6–10; Delbarre et al. (1995) *Int. J. Microcirc. Clin. Exp.* 15 (suppl. 1): 27–33; Bouskela et al. (1995) *Int. J. Microcirc. Clin. Exp.* 15 (suppl. 1):22–6; and Friesenecker et al. (1995) *Int. J Microcirc. Clin. Exp.* 15 (suppl. 1):17–21. The combination of diosmin and hesperidin is also useful for treating hemorrhoids. U.S. Pat. No. 5,858,371. A diosmin derivative retains at least one of these activities.

In certain embodiments, the combination of a tocopherol and a synergist or additional compound suitable for ameliorating the injury(ies) or disruption of energy metabolism secondary to stress can include flavonoids, including, but not limited to, rutin, hesperedin, diosmin and pycnogenol. Rutin acts synergistically with alpha-tocopherols and gamma-tocopherols. Hesperedin and diosmin each act synergistically with alpha-tocopherols. Pycnogenol acts synergistically with alpha-tocopherols. Pycnogenol, obtained from the pine bark, is a standardized extract composed of a mixture of flavonoids. Packer et al. (1999) *Free Radic. Biol. Med.* 27:704–724.

The invention also encompasses optimized formulations of a tocopherol and an additional compound. This additional compound can be, as non-limiting examples, daidzein or biochanin A. One preferred optimized formulation comprises daidzein and alpha-tocopherol or (+/−)-alpha-tocopherol. The formulations are optimized in that various combinations (e.g., ratios and concentrations) of a tocopherol and the additional compound are tested for activity. Any of the various assays described herein can be used to empirically determine specific optimized concentrations or ratios. The formulations with the highest activity (e.g., ability to prevent cell death in the presence of a metabolic inhibitor or other poison) can be considered optimized. Alternatively, optimized formulations can be predicted based on activities of the individual compounds and limited information on their use in combination.

Compounds particularly suited for development of optimized formulations with tocopherols include daidzein and biochanin A. A preferred optimized formulation comprises daidzein and alpha-tocopherol or (+/−)-alpha-tocopherol. Both daidzein and biochanin A are isoflavones, a class of flavonoids which can be isolated from plant material. For descriptions of the isolation of these isoflavones from plant material, see, for example, Hosny et al. (1999); Walz (1931); Wong (1962); and Pope et al. (1953). Both daidzein and biochanin A have a variety of properties, including anti-oxidant activity and anti-cancer properties. See, for example, Arora et al. (1998); Hodgson et al. (1999); Lyn-Cook et al. (1999); Hammons et al. (1999); Yin et al. (1999); and Toda et al. (1999).

Also suitable for the present invention are derivatives of daidzein or biochanin A. Such derivatives are structurally similar but non-identical to daidzein or biochanin A, but retain at least one activity of these compounds, such as anti-oxidant or anti-cancer activities. The derivatives can differ from daidzein or biochanin A, as non-limiting examples, by addition, substitution, or re-arrangement of hydroxyl, alkyl or other group. Derivatives of these compounds include those obtained by modifications including, but not limited to, glycosylation, methoxylation, halogenation, conjugation with proteins, or addition of other another moiety, such as a sugar or carbohydrate or alkyl, or moiety comprising oxygen, nitrogen, sulfur and/or phosphorus. Derivatives of daidzein and biochanin A also include salts thereof. Other derivatives can be in the form of prodrugs. Various derivatives of daidzein and biochanin A are known in the art and described in, for example, Arora et al. (1998); Boersma et al. (1999); Lapcik et al. (1997); Joannou et al. (1995); Keung (1993); Smit et al. (1992); Shao et al. (1980); and King et al. (1998).

The present invention relates to a composition comprising a tocopherol or derivative and a synergist or additional compound, where the synergist is a lactoferrin or derivative, or hesperetin or derivative. The composition can comprise tocopherol and synergist in the following ratios (w/v) or tocopherol:synergist: at least about 1:10,000, at least about 1:1000, at least about 1:100, at least about 1:10, at least about 1:3, at least about 1:1, at least about 3:1, at least about 10:1, at least about 100:1, at least about 1000:1, or at least about 10,000:1. Alternatively, the composition can comprise tocopherol and synergist in the following ratios (w/v) or tocopherol:synergist: no more than about 1:10,000, no more than about 1:1000, no more than about 1: 100, no more than about 1:10, no more than about 1:3, no more than about 1:1, no more than about 3:1, no more than about 10:1, no more than about 100:1, no more than about 1000:1, or no more than about 10,000:1. For lactoferrin, it is preferred that the ratios be at least about 1:1, preferably at least about 1:3, and most preferably at least about 1:10. A composition comprising diosmin as a synergist can comprise, for example, a unit dose containing greater than 1, greater than 10, greater than 100, greater than 200, or greater than 500 mg of diosmin; or no more that about 100, 200, 500, 1000, 2000, 5000, or 10,000 mg of diosmin. Typical doses are from 100 to 900 mg of diosmin, as exemplified in U.S. Pat. No. 5,849,786. However, suitable ratios and amounts of various tocopherols and synergists can be determined based on laboratory experiments to determine efficacy, as described herein. Typical doses for daidzein and biochanin A are known in the art and described in, for example, King et al. (1998); Irvine et al. (1998) *Am. J Clin. Nutr.* 68:1462S–1465S; Blair et al. (1996) *J. Cell. Biochem.* 61: 629–37; Nestel et al. (1999) *J. Clin. Endocrinol. Metab.* 84: 895–8; Pelissero et al. (1996) *J. Steroid. Biochem. Mol. Biol.* 57: 215–23.

The ratio of tocopherol:synergist will be such that the composition allows an amelioration of at least one stress secondary to alteration in energy metabolism, which is defined and which can be measured as described herein.

The composition can comprise at least about 0.3, at least about 1, at least about 3, at least about 10, at least about 25, at least about 50, at least about 100, at least about 200, at least about 400, at least about 500, at least about 1000, at least about 2000, at least about 4000, at least about 5000, at least about 10,000 µg/ml of tocopherol. Alternatively, the composition can comprise no more than about 0.3, no more than about 1, no more than about 3, no more than about 10, no more than about 25, no more than about 50, no more than about 100, no more than about 200, no more than about 400, no more than about 500, no more than about 1000, no more than about 2000, no more than about 4000, no more than about 5000, no more than about 10,000 µg/ml of tocopherol. Preferably, the composition comprises at least about 0.3, preferably at least about 1, more preferably at least about 5, more preferably at least about 10 µg/ml tocopherol. The composition can comprise at least about 0.3, at least about 1, at least about 3, at least about 10, at least about 25, at least about 50, at least about 100, at least about 200, at least about 400, at least about 500, at least about 1000, at least about 2000, at least about 4000, at least about 5000, at least about 10,000 µg/ml of synergist. Alternatively, the composition can comprise no more than about 0.3, no more than about 1, no more than about 3, no more than about 10, no more than about 25, no more than about 50, no more than about 100, no more than about 200, no more than about 400, no more than about 500, no more than about 1000, no more than about 2000, no more than about 4000, no more than about 5000, no more than about 10,000 µg/ml of tocopherol. Preferably, the composition comprises at least about 0.3, preferably at least about 1, more preferably at least about 5, more preferably at least about 10 µg/ml synergist. Exemplary ratios include, but are not limited to, a ratio of 33:1, 10:1, 3.3:1 or 1.1:1 (w/v) lactoferrin to alpha-tocopherol; a ratio of 1:1 (w/v) diosmin to alpha-tocopherol; a ratio of 1:2 (µM:µg/ml) of hesperetin to an alpha-tocopherol; a ratio of 250:1 (µM:µg/ml) of hesperetin to a delta- or gamma-tocopherol; a ratio of 15:1 or 5:1 (w/v) biochanin A to alpha-tocopherol; and a ratio of 15:1, 5:1, or 1.5:1 (µM:µg/ml) daidzein to alpha-tocopherol.

In general, synergistic and optimized doses of the present invention are established by determining the concentrations of compounds that provide the desired effect in a test system, such as the cell systems described in Example 1 herein. Based on such data, efficacious doses for administration to human (or other animal) subjects can be determined, for example, based on known or routinely ascertainable pharmacokinetics of the specific compound in humans (See, e.g., Benet, L.Z., et al., in *Goodman and Gilman's The Pharmacological Basis of Therapeutics,* Ninth Ed., Hardman, J. G., et al., eds., McGraw-Hill, San Francisco, 1996; Wagner, J. G., *Pharmacokinetics for the Pharmaceutical Scientist.* Technomic, Inc., Lancaster, Pa., 1993; Rowland, M., and Tozer, T. N., *Clinical Pharmacokinetics: Concepts and Applications,* 3$^{rd}$ ed., Lea & Febiger, Philadelphia, 1995).

The composition can also, as necessary, further comprise a suitable pharmaceutical carrier, as described below. In addition, the tocopherol and/or synergist and/or additional compound can be in the form of a pharmaceutically acceptable salt, as described below.

Methods of Identifying Compositions

Various methods can be employed for identifying non-naturally-occurring compositions comprising a tocopherol and a synergist or additional compound which ameliorate injury(ies) or disruption of energy metabolism secondary to stress. In general, cells (or cell lines), organs or organisms (collectively termed "subjects") are used which undergo the aerobic path of metabolism (oxidative metabolism or respiration); these are also termed "energy-competent" or "oxidatively competent." These subjects are perturbed, for example, by an introduction of a chemical or other change in environment which disrupts their oxidative metabolism. Normally, this would lead to a physically manifested and measurable stress or injury to the cell, such as cell death, increased membrane permeability, excessive production of free radicals (reactive oxygen species), or inhibition of enzyme activity. Subjects undergoing stress are also treated with test compounds (e.g., various formulations of compositions of tocopherol and a synergist or optimized formulations of a tocopherol and an additional compound), and stress is measured to determine the anti-stress efficacy of particularly compositions such as particular concentrations and ratios of tocopherol and synergist or additional compound.

Cell lines and organs which undergo oxidative respiration are particularly suitable for the present invention. This is because most of the cells of the body undergo oxidative respiration. In contrast, most cells and cell lines experimentally used in laboratories do not undergo oxidative respiration, but simple anaerobic respiration (fermentation). Thus, they are not accurate model systems for cellular activities in most organisms such as mammals. Examples of energetically-competent cell lines include, but are not limited to, GCL1 liver cells (Wif-B), as described in Example 1. Subjects can be experimentally subjected to various stresses, including without limitation hypothermia, hyperthermia, hypoxia, ionizing radiation, chemical insult, drug toxicity, injuries related to chemotherapy, exposure to toxins, physical exertion (in the case of tissues or organisms, e.g., from excessive exercise), aging, ischemia, transplantation, stroke, traumatic injury, and chemical and/or physical injuries due to pre-surgical or post-surgical preparations. Methods of induction of these various stresses are known in the art. Chemical insults include mitochondrial poisons and metabolic inhibitors. Chemicals also include those which induce ischemia, such as antimycin A, DNP, and IAA, the use of which are explicated in Examples 2.C, 2.D and 2.E, respectively. The level of injury due to the stress (and also the ability of a composition to ameliorate this injury) can be measured in a number of ways. Exemplary techniques include use of DCF-DA, Alamar Blue, and DHR123, which measure the production of free radicals (reactive oxygen species), as described in Examples 2.A., 2.F.2., and 2.B, respectively. Cell viability can be measured using the SYTOX assay, described in Example 2.F.3, or the kit described in Example 2.F.4. Enzyme activity, such as that of lactate dehydrogenase, can be measured as described in Example 2.F.1. Additional methods of measuring stress and injury are known in the art.

As noted above, subjects in various experiments to determine efficacy of compositions can be cells, tissues, organs or organisms. Organ-based assays include without limitation the use of isolated rat hearts (Example 3.A.) and isolated perfused rat livers (3.B.). Example 3.C. describes the use of rat heart hypothermic preservation. These assays are particularly useful for evaluating the activity of cardioplegic and organ preservation solutions comprising a composition of the invention. Organismal level assays include the infarction assay described in Example 4. As described in these examples, amelioration injury(ies) or disruption of energy metabolism secondary to stress can be quantified (e.g., by measuring changes in levels of fluorescence of markers indicating enzyme activity or cell death). Preferably, amelioration mediated by the compositions of this invention are at least about 30%, preferably at least about 50%, more preferably at least about 70%, even more preferably at least about 80%, and even more preferably at least about 90%.

It will be clear to one of skill in the art that additional assays, based on various cells, tissues, organs and organisms will be useful in identifying compositions comprising a tocopherol and a synergist such as hesperetin, diosmin or lactoferrin or optimized formulations comprising a tocopherol and an additional compound such as daidzein or biochanin A, which are useful in ameliorating injury(ies) or disruption of energy metabolism secondary to stress.

Methods of Making Compositions of the Invention

The compositions of the present invention comprise at least one tocopherol and a synergist, where the synergist is a flavonoid, such as hesperetin, diosmin or lactoferrin, or optimized formulations comprising a tocopherol and an additional compound such as a flavonoid, exemplified herein by daidzein or biochanin A. Suitable ratios and concentrations of these components are described above and are exemplified in the Examples. In a non-limiting example of the preparation of a composition of the invention, a tocopherol stock can be prepared by emulsification (e.g., by mixture with a bile salt); this can be combined with an aqueous solution of hesperetin (e.g., in an organic solvent, and diluted in a buffer) or lactoferrin (in a suitable buffer such as a salt or buffer). As a specific, non-limiting example, a tocopherol stock can be prepared in glycocholic acid, a bile salt. This stock can comprise, for example, at least about 10, at least about 20, at least about 40, at least about 100, or at least about 200 mg/ml tocopherol. The glycocholic acid can be at a concentration of at least about 1, at least about 5, at least about 10, at least about 20, at least about 40, or at least about 100 mM. A hesperetin stock can be prepared in a solvent such as DMSO (dimethyl sulfoxide) and then diluted in a buffer such as HEPES. This stock can comprise, for example, at least about 10, at least about 20, at least about 40, at least about 100, or at least about 200 mg/ml hesperetin. Portions of the tocopherol and hesperetin stocks can then be mixed to achieve a desired ratio and concentration of agents. Similarly, a stock of lactoferrin can be prepared by dilution in a suitable buffer (such as physiological saline or HEPES). This stock can comprise, for example, at least about 10, at least about 20, at least about 40, at least about 100, or at least about 200 mg/ml lactoferrin. A portion of this stock can then be combined with a portion of the tocopherol stock to achieve a desired ratio and concentration of agents.

Alternative formulations can also be prepared. While there is no motivation in the art to do so, additional mixtures comprising a tocopherol and a synergist or additional compound can be prepared based on published reports describing the separate preparation of solutions comprising tocopherol (U.S. Pat. Nos. 5,897,879; 5,891,923; 5,880,148; 5,827,878; 5,773,026; 5,770,222; 5,763,423; 5,759,566; 5,692,302; 5,637,315; 5,610,180; 5,480,645; 5,455,055; 5,393,513; 5,384,115; 5,364,632; 5,364,631; 5,336,485; 5,326,757; 5,301,664; 5,198,432; 5,179,122; 5,114,957; 5,051,406; 5,023,271; and McGee et al. (1990) *J. Parent. Enter. Nutr.* 14:74–78), solutions comprising lactoferrin (U.S. Pat. Nos. 5,869,446; 5,861,491; 5,834,424; 5,712,247; 5,576,299; 5,561,109; 5,543,392; 5,330,975; 5,240,909; and 5,214,028), solutions comprising hesperetin (U.S. Patent Nos. 5,587,176; and 5,763,414); and solutions comprising diosmin [Dumon et al. (1994); Feneix-Clerc et al. (1994); Kavutcu et al. (1999); Melzig et al. (1999); Teel et al. (1998); and Ciolino et al. (1998)].

The preparation of the compositions of the present invention is slightly complicated by the fact that tocopherols are generally hydrophobic (lipophilic), while lactoferrin and hesperetin are hydrophilic (lipophobic). While the composition can be administered or ingested in two doses (e.g., an aqueous phase comprising the synergist or additional compound, and a non-aqueous phase comprising the tocopherol), it is preferable that the tocopherol and synergist or additional compound be combined and mixed together into the same solution. Suitable for preparation of these mixed compositions are any of a number of techniques known in the art useful for preparing aqueous solutions comprising hydrophobic active ingredients. Such techniques include the addition of surfactants and non-evaporated co-solvents or preparation of an emulsion or microemulsion, liposomes or colloidal particles. U.S. Pat. Nos. 5,571,534; and 5,531,925. Alternatively, U.S. Pat. No. 5,891,845 provides a method for administration of tocopherols using liquid crystal structures. Hydrophobic compounds can be stabilized in aqueous solutions by addition of serum proteins (e.g., human serum albumin) or bile salts. U.S. Pat. Nos. 5,643,566; and 5,616,342. Other methods for preparing therapeutic compositions comprising hydrophobic ingredients are described in U.S. Pat. Nos. 5,824,668; and 5,733,526. These patents generally allow the mixture of hydrophobic and hydrophilic ingredients into the same composition. In addition to aqueous solutions, hydrophilic and hydrophobic compounds can be administered together as a cream or lotion. U.S. Pat. No. 5,422,361. Methods of preparing other compounds described herein are also known in the art. Methods of preparing daidzein and biochanin A and foods containing them are described in, for example, U.S. Pat. Nos. 5,733,926; and 5,830,887.

In an alternative technique, a tocopherol useful in the present invention can be rendered hydrophilic by modification, e.g., addition of hydrophilic moieties such as hydroxyl groups, or conjugation to hydrophilic moieties such as sugars. An aqueous solution of this water-soluble tocopherol (e.g., in a buffer or salt such as physiological saline) can then be readily combined with aqueous solutions of hesperetin, diosmin or lactoferrin.

Mixtures comprising a tocopherol and a synergist or additional compound can be incorporated into any of various media, including, but not limited to exemplary nutritional suuplements listed below:

Functional food ingredients. The formulations can be used, for example, as ingredients in high-energy sports foods and drinks designed for athletes. These include concentrated carbohydrate gels, such as those containing maltodextrin and designed to be consumed with water. Additional foods include, but are not limited to, food bars, beverages, powders, cereals, cooked foods, food additives and candies.

Functional companion animal foods. These include foods for pets and sports animals.

Optimal animal feeds.

Wellness dietary supplements to maintain health and improve probable outcome. These may be ingested, for example, as a prophylactic by a human who suspects he or she may be in future danger of a stress (e.g., at high risk for coronary disease). The formulation is designed to reduce the seriousness or damage caused by a coronary infarction subsequent to ingestion. The formulation can also be ingested by individuals who await a future organ transplant.

Medical foods. These includes foods designed for both nutritional and therapeutic functions. The formulations include medical foods which are scientifically formulation, those which are ingested under prescription, and those which are administered via intubation.

Baby foods.

Other uses of the mixtures of the invention include:

Organ preservation solutions. These can be used for preservation of blood, bone, cornea, heart, intestine, kidney, liver lung, skin, or other tissues. These can also be used for applications such as transplant, and organ preservation during surgery.

Cardioplegic solutions.

Crop protectants.

Guiding assay for development of plant or animal traits.

Chemotherapy protective agents.

Chemotherapy agents, antineoplastics (which select tocopherols which increase sensitivity to stress).

Formulations comprising tocopherols capable of reducing injury(ies) or disruption of energy metabolism secondary to stress can be introduced into any of these applications.

Methods of preparing these various media (animal feeds, sports drinks, cardioplegic solutions, etc.) are known in the art. For example, preparation of animal feeds is described in U.S. Pat. Nos. 4,904,486; 5,759,598; 5,897,886; 5,904,928; and 5,744,186; preparation of dietary supplements, U.S. Pat. Nos. 4,973,467; 4,980,168; 5,051,258; U.S. Pat. No. RE 33,988; U.S. Pat. Nos. 5,219,889; 5,248,503; and 5,487,894; preparation of medical foods, U.S. Pat. Nos. 5,260,279; 5,326,569; 5,550,146; 5,587,399; and 5,629,023; preparation of baby foods, U.S. Pat. Nos. 5,397,591; 5,723,166; 5,840,361; preparation of organ preservation solutions, U.S. Pat. No. 4,938,961; preparation of cardioplegic solutions, U.S. Pat. Nos. 4,988,515 and 5,554,497; preparation of crop protectants, U.S. Pat. No. 5,753 ,591; preparation of chemotherapy protective agents, U.S. Pat. Nos. 5,808,140 and 5,840,759; and preparation of chemotherapy agents, U.S. Pat. Nos. 5,736,531; 5,770,591; 5,776,898; 5,808,038; and 5,859,295. See also the references cited therein. The preparation of a variety of medicinal excipients is described, for example, in *Remington's Pharmaceutical Sciences,* 18th edition, Mack Publishing (1990). The preparation of aqueous solutions of tocopherol and a synergist or additional compound is described above. Such aqueous solutions can be used directly as medicinal agents (i.e., injected directly into a human being), or added to these various media, as is known in the art. Other methods of addition of compositions of the invention to other media can be accomplished by methods known in the art. For example, U.S. Pat. No. 5,650,185 describes preparation of oils comprising tocopherols, which can be used in food preparation. Also, U.S. Pat. No. 5,296,464 describes the addition of lactoferrin to animal feeds. U.S. Pat. No. 5,763,414 describes preparation of laboratory animal feed comprising hesperetin.

Methods of Using Compositions and Formulations of the Invention

The compositions comprising a tocopherol and/or derivative thereof and a synergist such as hesperetin, diosmin and/or lactoferrin, and/or derivatives thereof, or an optimized formulation comprising a tocopherol and an additional compound such as daidzein or biochanin A, are administered to a subject to obtain a cytoprotective effect.

The subject may be experiencing a disruption of energy metabolism secondary to stress, experiencing a stress that can disrupt energy metabolism, or be at risk for disruption of energy metabolism secondary to stress. The compositions, as described above, can be prepared as a medicinal preparation (such as an aqueous solution for injection) or in various other media, such as foods or humans or animals.

If administered as a medicinal preparation, the composition can be administered, either as a prophylaxis or treatment, to a patient in any of a number of methods. The cytoprotective compositions may be administered alone or in combination with other pharmaceutical agents and can be combined with a physiologically acceptable carrier thereof. The effective amount and method of administration of the particular cytoprotective formulation can vary based on the individual subject, the stage of disease, the stage of disruption of energy metabolism and other factors evident to one skilled in the art. During the course of the treatment, the concentration of the subject compositions may be monitored to insure that the desired level is maintained.

Generally, the route(s) of administration useful in a particular application are apparent to one of skill in the art. Routes of administration include, but are not limited to, oral, topical, dermal, transdermal, transmucosal, intranasal, intraventricular, epidermal, parenteral, or gastrointestinal.

For in vitro or ex vivo administration, the compounds may be provided in the medium of the cells and/or organ, as a single bolus, by repetitive addition, by continual infusion, or the like.

For administration, the invention includes subject compositions suitable for oral administration including, but not limited to, pharmaceutically acceptable tablets, capsules, powders, solutions, dispersions, or liquids. For rectal administration, the subject compositions may be provided as suppositories, as solutions for enemas, or other convenient application. Otherwise, the subject compositions may be administered intravascularly, arterially or venous, subcutaneously, intraperitoneally, intraorganally, intramuscularly, or the like.

For administration, the formulations may conveniently be presented in unit dosage form and may be prepared by any method well known in the art of pharmacy. Such methods include the step of bringing into association the active ingredients with the carrier which constitutes one or more accessory ingredients. In general, the formulations are prepared by uniformly and intimately bringing into association the active ingredients with liquid carriers or finely divided solid carriers or both, and then if necessary shaping the product.

For oral administration, suitable subject compositions include, but not limited to, pharmaceutically acceptable tablets, capsules, powders, solutions, dispersions, or liquids. Also, the subject compositions may be compounded with other physiologically acceptable materials which can be ingested including, but not limited to, foods, including, but not limited to, food bars, beverages, powders, cereals, cooked foods, food additives and candies.

When the composition is incorporated into various media such as foods, it may simply be orally ingested. The food can be a dietary supplement (such as a snack or wellness dietary supplement) or, especially for animals, comprise the nutritional bulk (e.g., when incorporated into the primary animal feed).

The amount of the composition ingested, consumed or otherwise administered will depend on the desired final concentration. Typically, the amount of a single administration of the composition of the invention can be about 0.1 to about 1000 mg per kg body weight, or about 0.1 to about 1000 mg per day. The amount of a single dosage can be, for example, at least about 10, at least about 20, at least about 25, at least about 30, at least about 50, at least about 100, at least about 125, at least about 150, at least about 200, at least about 250, at least about 300, at least about 350, at least about 400, or at least about 500 $mg/m^2$ body surface area. The dosage can also be less than about 500, less than about 400, less than about 350, less than about 300, less than about 250, less than about 200, less than about 150, less than about 100, less than about 50, less than about 30, less than about 25, less than about 20, or less than about 10 $mg/m^2$. Preferably, the dosage is at least about 200 $mg/m^2$. Also, preferably the dosage is less than about 300 $mg/m^2$. Any of these doses can be further subdivided into separate administrations, and multiple dosages can be given to any individual patient. A typical dosage for vitamin E administration is 100–600 mg/kg/day for an adult human. However, various different dosages are described in scientific publications; see, for example, Ng et al. (1999) *Food Chem. Toxicol.* 37: 503–8; Ko et al. (1999) *Arch. Phys. Med. Rehabil.* 80: 964–7; Chen et al. (1999) *Prostaglandins Other Lipid Mediat.* 57: 99–111; and Thabrew et al. (1999) *Ann. Clin. Biochem.* 36: 216–20.

In general, synergistic and optimized doses of the present invention are established by determining the concentrations of compounds that provide the desired effect in a test system, such as the cell systems described in Example 1 herein, or in other suitable in vitro or in vivo model systems. Based on such data, efficacious doses for administration to human (or other animal) subjects can be determined, for example, based on known or routinely ascertainable pharmacokinetics of the specific compound in humans (See, e.g., Benet, L. Z., et al., in *Goodman and Gilman's The Pharmacological Basis of Therapeutics*, Ninth Ed., Hardman, J. G., et al., eds., McGraw-Hill, San Francisco, 1996; Wagner, J. G., *Pharmacokinetics for the Pharmaceutical Scientist*. Technomic, Inc., Lancaster, Pa. 1993; Rowland, M., and Tozer, T. N., *Clinical Pharmacokinetics: Concepts and Applications*, $3^{rd}$ ed., Lea & Febiger, Philadelphia, 1995).

To determine the optimum concentration for any application, conventional techniques may be employed. Thus, for in vitro and ex vivo use, a variety of concentrations may be used and various assays employed to determine the degree of dysfunction of the cells when exposed to stress. Examples of such assays are described herein and have been described, for example, in U.S. Pat. No. 5,801,159.

Formulations of the present invention adapted for oral administration may be presented as discrete units such as capsules, cachets or tablets each containing a predetermined amount of the active ingredients; as a powder or granules; as a solution or a suspension in an aqueous or non-aqueous liquid; or as an oil-in-water liquid emulsion or a water-in-oil liquid emulsion. The active ingredients may also be presented as a bolus, electuary or paste.

A tablet may be made by compression or moulding, optionally with one or more accessory ingredients. Compressed tablets may e prepared by compressing in a suitable machine the active ingredient in a free-flowing form such as a powder or granules, optionally mixed with a binder (e.g. povidone, gelatin, hydroxypropylmethylcellulose), lubricant, inert diluent, preservative, disintegrant (e.g. sodium starch glycollate, cross-linked povidone, cross-linked sodium carboxymethylcellulose) surface-active or dispersing agent. Moulded tablets may be made by moulding in a suitable machine a mixture of the powdered compound moistened with an inert liquid diluent. The tablets may optionally be coated or scored and may be formulated so as to provide controlled release of the active ingredients therein using, for example, hydroxypropylmethylcellulose in varying proportions to provide the desired release profile.

The subject compositions may be administered parenterally including intravascularly, arterially or venous, subcutaneously, intradermally, intraperitoneally, intraorganally, intramuscularly, cerebroventricularly, intranasally, or the like.

Formulations for parenteral administration include aqueous and non-aqueous isotonic sterile injection solutions which may contain buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose sealed containers, for example, ampules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Compositions of the present invention may be used with medicinal products such as organ preservation solutions, cardioplegic solutions and chemotherapy protective agents. Administration of chemotherapy protective agents is described, for example, in U.S. Pat. Nos. 5,808,140 and 5,840,759.

With regard to organ preservation, it is generally understood that "living" organs, including the heart, continue the process of metabolism after removal from the donor so that cell constituents are continuously metabolized to waste products. The accumulation of these metabolic waste products, depletion of cell nutrients and consequent derangement of cell composition lead to progressive loss of function and ultimately to cell death if the storage technique is inadequate and, for example, the organ will lose its ability to function adequately after transplantation into the recipient. Several procedures have been successfully explored to enable organs to be preserved ex vivo for useful time periods. In one method the organ to be transplanted is rapidly cooled by flushing cold organ preservation solutions through the organ's vascular system and maintaining the organ at temperatures near 0° C. for the purpose of greatly slowing the metabolic rate. In the case of the mammalian heart, the flush solution composition is designed to cause the heart to rapidly stop beating as well as to preserve it. Another method for organ storage utilizes continuous perfusion at temperatures in the range of 7°–10° C. with an oxygenated solution designed to support oxidative metabolism and to remove waste products. A suitable organ perservation perfusate is delivered through the circulatory system of the isolated organ—usually from the arterial side—and as the perfusate is conveyed through the vascular system waste products are carried away from the organ. Organs such as kidney, liver and pancreas can commonly be preserved for several days.

Cardioplegic solutions are chemical solutions designed to stop the heart and reduce its energy demands during cardiac surgery. Generally, cardioplegic solutions may be infused directly into the heart in order to either protect the heart against ischemic damage when its blood supply is interrupted (e.g., during routine open heart surgery) or to avoid or reverse ischemic damage to the heart which has been deprived of its blood supply (e.g., acute coronary occlusion) while such blood supply is re-established under controlled conditions (e.g., in the operating room or in the cardiac catheterization laboratory).

Generally, to be appropriate and effective, cardioplegic and organ preservation solutions have a composition that (1) minimizes hypothermic-induced cell swelling, (2) prevents intracellular acidosis, (3) prevents the expansion of extracellular space during the flush-out period, (4) prevents injury from oxygen-free radicals, especially during reperfusion, and (5) provides substrates for regenerating high-energy phosphate compounds during reperfusion.

Compositions of the present invention may be incorporated into cardioplegic and organ preservation solutions or may simply be administered along with such solutions. Cardioplegic and organ preservation solutions and methods for their administration are known in the art. See, for example, U.S. Pat. Nos. 4,798,824; 4,873,230; 4,879,283; 4,938,961; 4,988,515; 5,554,497. Additional recent documents related to and describing cardioplegic and other organ preservation solutions include, Muhlbacher et al. (1999) *Transplant. Proc.* 31: 2069–2070; Elwatidy et al. (1999) *Ann. Thorac. Surg.* 68: 447–453; Vento et al. (1999) *Ann. Thorac. Surg.* 68:413–420; Wieselthaler et al. (1999) *Transplant. Proc.* 31: 2067–2068; de Boer et al. (1999) *Transplant. Proc.* 31:2065–2066; Matsuda et al. (1999) *Surgery* 126: 264–271; Tanoue et al. (1998) *Cardiovasc. Surg.* 6: 622–628.

For example, compositions of the present invention may be used in conjunction with the preservation solution commonly known as "UW" solution which contains hydroxyethyl starch and is described in U.S. Pat. No. 4,879,283. This preservation solution is commercially available as VIASPAN™ (Dupont Pharmaceuticals).

For topical administration, the subject compositions may be provided as a wide variety of product types including, but are not limited to, lotions, creams, gels, sticks, sprays, ointments and pastes. These product types may comprise several types of formulations including, but not limited to solutions, emulsions, gels, solids, and liposomes.

Compositions useful for topical administration of the compositions of the present invention formulated as solutions typically include a pharmaceutically-acceptable aqueous or organic solvent. The terms "pharmaceutically-acceptable organic solvent" refer to a solvent which is capable of having a tocopherol, and the synergist or additional compound dispersed or dissolved therein, and of possessing acceptable safety properties (e.g., irritation and sensitization characteristics). Examples of suitable organic solvents include: propylene glycol, polyethylene glycol (200–600), polypropylene glycol (425–2025), glycerol, 1,2, 4-butanetriol, sorbitol esters, 1,2,6-hexanetriol, ethanol, isopropanol, butanetriol, sorbitol esters, 1,2,6-hexanetriol, ethanol, isopropanol, butanediol, and mixtures thereof.

If the topical compositions useful in the subject invention are formulated as an aerosol and applied to the skin as a spray-on, a propellant is added to a solution composition. Examples of propellants useful herein include, but are not limited to, the chlorinated, fluorinated an chloro-fluorinated lower molecular weight hydrocarbons.

Topical compositions useful in the subject invention may be formulated as a solution comprising an emollient. Such compositions may comprise a lipid soluble salt of hesperetin, such as a calcium salt. As used herein, "emollients" refer to materials used for the prevention or relief of dryness, as well as for the protection of the skin. A wide variety of suitable emollients are known and may be used herein.

Another type of product that may be formulated from a tocopherol and synergist or additional compound solution is a cream. Another type of product that may be formulated from a subject solution is a lotion.

Yet another type of product that may be formulated from a tocopherol and synergist or additional compound is an ointment. An ointment may comprise a simple base of animal or vegetable oils or semi-solid hydrocarbons (oleaginous). Ointments may also comprise absorption ointment bases which absorb water to form emulsions. Ointment carriers may also be water soluble.

Another type of formulation is an emulsion. Emulsifiers may be nonionic, anionic or cationic and examples of emulsifiers are described in, for example, U.S. Pat. Nos. 3,755,560, and 4,421,769.

Lotions and creams can be formulated as emulsions as well as solutions.

Single emulsions for topical preparations, such as lotions and creams, of the oil-in-water type and water-in-oil type are well-known in the art. Multiphase emulsion compositions, such as the water-in-oil-in-water type, are also known, as disclosed, for example, in U.S. Pat. No. 4,254,105. Triple emulsions are also useful for topical administration of the present invention and comprise an oil-in-water-in-silicone fluid emulsion as disclosed, for exampled in U.S. Pat. No. 4,960,764.

Another emulsion useful in the topical compositions is a micro-emulsion system. For example, such a system comprises from about 9% to about 15% squalane; from about 25% to about 40% silicone oil; from about 8% to about 20% of a fatty alcohol; from about 15% to about 30% of polyoxyethylene sorbitan mono-fatty acid (commercially available under the trade name TWEENS) or other nonionics; and from about 7% to about 20% water.

Liposomal formulations are also useful for the compositions of the present invention. Such compositions can be prepared by first combining a tocopherol, and an additional compound, such as a synergist, with a phospholipid, such as dipalmitoylphosphatidyl choline, cholesterol and water according to known methods, for example, as described in Mezei et al. (1982) *J. Pharm. Pharmacol.* 34:473–474, or a modification thereof Epidermal lipids of suitable composition for forming liposomes may be substituted for the phospholipid. The liposome preparation is then incorporated into one of the above topical formulations (for example, a gel or an oil-in-water emulsion) in order to produce the liposomal formulation. Other compositions and pharmaceutical uses of topically applied liposomes are described for, example, in Mezei (1985) *Topics in Pharmaceutical Sciences,* Breimer et al. eds., Elsevier Science, New York, N.Y., pp. 345–358.

For rectal administration, the subject compositions may be provided as solutions for enemas, as suppositories with a suitable base comprising, for example, cocoa butter or a salicylate, or as other convenient applications.

Formulation for vaginal administration may be presented as pessaries, tampons, creams, gels, pastes, foams or spray formulations containing in addition to the active ingredient such carriers as are known in the art to be appropriate.

To determine the optimum concentration for any application, conventional techniques may be employed. Thus, for in vitro and ex vivo use, a variety of concentrations may be used and various assays employed to determine the degree of dysfunction of the cells when exposed to stress. Examples of such assays are described herein and have been described, for example, in U.S. Pat. No. 5,801,159.

For preservation of cells, the subject compositions may be added for a short time, usually at least about 0.5 hour and then removed, maintained for long periods of time with the cells, including weeks or months or longer, may be replenished periodically, or the like. Since the subject compounds are for the most part safe, without significant side effects, the subject compounds may be maintained for the entire stress period or for an extended period in anticipation of stress.

In some situations, oxygen deprivation or other stress may due to physical activity, for example, with exercise or sports activities, or to surgery. The subject compositions may be formulated as foods, as described above. The subject compositions may combined with particular foods to enhance their effectiveness, such as high protein foods, foods which enhance transport across the gut, such as gums, foods which provide for compatible energy sources, and the like.

The above-mentioned compositions and methods of administration are meant to describe but not limit the methods of administering the cytoprotective compositions of the invention. The methods of producing various compositions and devices are within the ability of one skilled in the art and are not described in detail here.

The methods and compositions of the present invention are related to compositions comprising tocopherol which are capable of ameliorating injury(ies) or disruption of energy metabolism secondary to stress. These disruptions can be induced experimentally by chemical interference (e.g., by using toxins such as antimycin or iodoacetate) or by changing the environmental conditions in the laboratory (e.g., by inducing anoxia, hypothermia, hyperthermia, etc.).

Various assays, compositions and methods useful for identifying compositions for amelioration of disruption of energy metabolism secondary to stress are described in Examples 1 to 4.

The efficacies of various tocopherol isomers are described in Example 5. The effect of salts on tocopherol efficacy is described in Example 6.

Synergistic mixtures identified using these methods include mixtures of tocopherol isomers and mixtures of tocopherols and non-tocopherols. Examples of the former include mixtures of gamma- and alpha-tocopherol (as described in Example 7). Examples of the latter include mixtures of tocopherol and lactoferrin (as described in Examples 8). Example 9 describes synergistic mixtures of tocopherols and diosmin.

Example 10 illustrates the determination of an optimized formulation comprising biochanin A and a tocopherol. Example 11 illustrates the determination of an optimized formulation comprising daidzein and alpha-tocopherol or (+/−)-alpha-tocopherol. Example 12 describes synergistic combinations of hesperetin and various tocopherols.

The following examples are provided to illustrate, but not limit, the invention.

EXAMPLES

Example 1

Example 1 describes methods for culturing exemplary oxidatively (energetically) competent cells for use in cellular assays described herein.

GCL1 Cell Culture

The GCL1 (WiF-B) liver cell line is a hybrid originating from the fusion of rat hepatoma cells (fao) and human fibroblasts (W138). Cassio et al. (1991) *J. Cell Biol.* 115:1397–1408; Shanks et al. (1994) *J. Cell Science* 107:813–825. When GCL1 cells are cultured under optimal conditions they attain maximal density in a monolayer and exhibit structural and functional characteristics of a polarized hepatocyte. Ihrke et al. 1993, *J. Cell Biol.* 123:1761–1775. At greater than 80% confluence, more than 80% of the cells participate in forming one or more phaselucent, spherical structures that are located between cells, termed bile canicular-like spaces. In contrast to the majority of cell lines maintained in culture which are fermentative, GCL1 cells, when at their maximal density and polarity, are highly oxidative (i.e., they can be readily killed by inhibitors of oxidative phosphorylation or electron transport uncouplers). Such cells grown under such conditions are useful for screening compounds and chemical libraries to identify cytoprotective tocopherols that may be useful to treat ischemic injury. These cells are amenable to use in high throughput screening (HTS) technology.

GCL1 growth media is a modified F-12 Casio Nutrient Mixture (Gibco BRL Cat. # 94-5147EL). Other reagents used in the culture of GCL1 cells include 0.05% trypsin solution, Phosphate Buffered saline (PBS; Irvine Scientific Cat. # 9240) and Fetal Bovine Serum (FBS; Hyclone # SH30070.03).

The GCLI cell line, obtained from Johns Hopkins University, and passage numbers 3 to 9 are stored frozen. Frozen GCL1 cells are thawed rapidly (within 60– 80 seconds) in a 37° C. water bath. As soon as the ice is melted, the vial is removed from the water bath and the cell suspension is transferred to 25 ml of growth media in a 75 cm$^2$ culture flask (T75; Corning 430641). The cells are evenly distributed in the growth media and are incubated at 37° C. with 7% $CO_2$ in air atmosphere. The GCL1 cell line grows in monolayers and takes approximately 7 days to reach confluence when seeded at $10^6$ cells per T75 flask. During this time the cells are microscopically examined and the growth media changed every 2 days. The culture media is pre-warmed before use.

Once the cells have reached confluence, they can be subcultured and used to seed either T75 flasks or opaque 96-well cell culture plates (Costar 3603 or 3916). The growth media is removed from the tissue culture flask(s) and the cells are carefully washed with PBS (approximately 20 ml for a T75 flask). The PBS is removed and replaced with 2 ml of 0.05% Trypsin solution. After 4–5 minutes at room temperature, or until the cells begin to loosen from the vessel surface, the flask is tapped gently to complete the cell detachment. The cell suspension is diluted with 8 ml of fresh growth media. The cells are counted using a hemocytometer and, from a confluent T75 flask, approximately $10^7$ cells are harvested.

To seed T75 flasks, $10^6$ cells are added to the flask and diluted with 25 mL of media. For 96-well plates, $10^6$ cells per plate at 200 $\mu$L/well (approximately $10^4$ cells/well) are seeded. To set up 96-well plates, a multichannel Pipettor (12-channel or automatic 8-channel) may be used to distribute the cell suspension. Before seeding into each plate, the cell suspension is mixed to ensure the cells are uniformly distributed. The growth media is replaced with 200 $\mu$L/well of fresh media plates every day with the exception of the day after the plates are seeded. The cells can be used for assays 6–8 days after they are seeded.

Example 2

Various protocols described below describe methods of using cellular assays to determine the ability of a potential biological tocopherol to counteract cellular stress.

Example 2.A.
Def-Da Reactive Oxygen Species (ROS) Assay

ROS generation and cell injury can be induced in cells by treatment with mitochondrial poisons or metabolic inhibitors, such as Antimycin A or $Ca^{2+}$. Kowaltowski et al. (1998) *FEBS Letters* 425:213–216; Kowaltowski et al. (1995) *Am. J. Physiol.* 269:C141–147; Kowaltowski et al. (1996) *J. Biol. Chem.* 271:2929–2934. This protocol allows the screening and evaluation of tocopherols to protect cells against chemical ischemia and cell injury, such as that induced through ROS generation. In this protocol, we have used mitochondrial poisons or metabolic inhibitors to induce ROS generation in oxidatively competent cells as a model system for cytoprotective tocopherol screening. This procedure is amenable to high-throughput screening (HTS) technology.

1. Assay for ROS 2,7-Dihydrodichlorofluorescein diacetate (DCF-DA) (Molecular Probes, Cat # D-399), a probe for intracelluar production of ROS, is a nonfluorescent ester that, upon penetration into cells, is hydrolyzed to DCFH by the cellular esterases. LeBel et al. (1992) *Chem. Res. Toxicol.* 5:227–231. The probe is rapidly oxidized to the highly fluorescent species dichlorofluorescein in the presence of cellular peroxidase and reactive oxygen metabolites such as hydrogen peroxide or fatty acid peroxides. The mitochondrial poisons or metabolic inhibitors KCN, Antimycin A (AA) or sodium iodoacetate (IAA) are used to induce ROS generation in the cells.

DCF-DA is dissolved in DMSO to generate a 100 mM stock solution, which is aliquoted and stored in dark at −20° C. until use. Oxidatively competent cells are seeded onto 96-well plates at 2.5×$10^3$ cells/well. Cells are grown in DMEM with 5% FBS and 1.5 g/L sodium bicarbonate for 24 hours to reach 85% confluent. Before treatment, cells are washed once with 200 $\mu$l warm HBSS (25 mM HEPES, 100 mM NaCl, 5 mM KCl, 1.2 mM $MgCl_2$, 1.3 mM $CaCl_2$, 1.0 mM $KH_2PO_4$, pH 7.4, filter sterilized). The 100 mM stock solution of non fluorescent diacetate ester of DCF-DA in DMSO is diluted in HBSS to yield a final concentration of 15 $\mu$M. 100 $\mu$l of this solution is added to all wells of the test plate and the plate is incubated at 37° C. for 30 minutes to allow incorporation and hydrolysis of the diester from the probe. After 30 minutes incubation, the HBSS containing DCF-DA is removed and replaced with 100 $\mu$l of HBSS containing different concentration of KCN (Sigma Chemical Co., Cat # 20,781-0), Antimycin A (Sigma, Cat #A8674) or sodium iodoacetate (Sigma, Cat #2512). KCN is dissolved in HBSS to make a stock solution of 1 M, then diluted further with HBSS to 50, 25, 12.5, 6.25 and 3.125 mM for dose-response curves. Antimycin A is dissolved in DMSO to make a stock solution of 50 mM, then diluted further with HBSS to 50, 25, 12.5, 6.25, and 3.125 $\mu$M for dose-response curves. Sodium Iodoacetate is dissolved in HBSS to make 100 mM stock solution, and then diluted further with HBSS to 100, 50, 25, 12.5, and 6.25 $\mu$M for dose-response curves.

For screening for cytoprotective tocopherols, the cells are then treated with cytotoxic and/or cytoprotective tocopherols after DCF-DA loading. $H_2O_2$ (10 mM) is used for generating 100% ROS in each experiment. Fluorescent measurements are made on Labsystem cytofluorometer plate reader at 485 nm excitation and 530 emission. The plates are kept at 37° C. in an incubator. The generation of intracellular ROS is measured every 30 minutes for 5 hours by automatic robot operation.

2. Cell Injury Measurement

Cell injury induced by ROS generation after treatment is measured by Alamar Blue stain. Alamar blue, an oxidation-reduction sensitive dye, is a fluorometric/colorimetric indicator of metabolic activity. Alamar Blue is non-toxic dye, making it possible to obtain measures of the metabolic rate and the maximal functional capacity of mitochondrial in living cells. At the 4 hour incubation time point, 20 μl of 1×Alamar Blue is added to each well and incubated for 60 minutes prior to measurement. The plates are read on a cytofluorometer at 540 nm excitation and 590 nm emission to determine the conversion of the colorimetric dye to a fluorometric reading. The data is compared to non-treated cells (control) and is expressed as mean±S.D from 4 culture wells.

3. Results

The data is reported as arbitrary fluorescence units of DCF. Results are mean+SD of net intracellular fluorescence unit, e.g., fluorescence in the presence of cytotoxic compound (AA, KCN or IAA) minus fluorescence without cytotoxic compound (HBSS only) in triplicate. Comparisons among groups are statistically evaluated by two-tailed t-test (Graphpad prism Software, version 2.0). Differences are considered significant at $P<0.05$.

Example 2.B
Peroxynitrite Anion ROS Assay

This protocol allows the screening and evaluation of tocopherols, synergists, and combinations thereof, to protect cells against chemical ischemia and cell injury, such as that induced through peroxynitrite formation. In this protocol, we have used mitochondrial poisons or metabolic inhibitors to induce peroxynitrite formation in oxidatively competent cells as a model system for cytoprotective tocopherol screening. This procedure is amenable to HTS technology.

1. Assay for Peroxynitrite

Dihydrorhodamine 123 (DHR 123) (Molecular Probes, Cat # D-632), a marker for peroxynitrite, is a nonfluorescent probe that enters to mitochondrial and fluoresces when oxidized by peroxynitrite to positively charged Rhodamine 123 derivative. The mitochondrial poisons or metabolic inhibitors KCN, Antimycin A (AA) or sodium iodoacetate (IAA) are used to induce peroxynitrite formation in the cells.

DHR 123 is dissolved in DMSO to generate a 50 mM stock solution, which is aliquoted and store in dark at $-20°$ C. until use. Oxidatively competent cells are seeded onto 96-well plates at $2.5 \times 10^3$/well. Cells are grown in DMEM with 5% FBS and 1.5 g/L sodium bicarbonate for 24 hours to reach 85% confluence. Before treatment, cells are washed once with 200 μl warm HBSS. The 50 mM stock solution of nonfluorescent DHR 123 in DMSO is diluted in HBSS to yield a final concentration of 3 μM. 100 μl of this solution is added to all wells of the test plate and the plate is incubated at 37° C. for 30 minutes. After 30 minutes incubation, the HBSS containing DHR 123 is removed and replaced with 100 μl of HBSS containing different concentration of KCN (Sigma, Cat #20,781-0), Antimycin A (Sigma, Cat # A8674) or sodium iodoacetate (Sigma, Cat #2512). KCN is dissolved in HBSS to make a stock solution of 1 M, then diluted further with HBSS to 50, 25, 12.5, 6.25 and 3.125 mM for dose-response curves. Antimycin A is dissolved in DMSO to make a stock solution of 50 mM, then diluted further with HBSS to 50, 25, 12.5, 6.25, and 3.125 μM for dose-response curves. Sodium Iodoacetate is dissolved in HBSS to make 100 mM stock solution, and then diluted further with HBSS to 100, 50, 25, 12.5, and 6.25 μM for dose-response curves.

For screening of cytoprotective tocopherols, the cells are then treated with the mitochondrial poisons or metabolic inhibitors and/or cytoprotective tocopherols after DHR 123 loading. Peroxinitrite is used to generate 100% Rhodamine 123 fluorescence in each experiment. The fluorescence of Rhodamine 123 is measured using a Labsystem cytofluorometer plate reader at 485 nm excitation and 530 emission. The plates are maintained at 37° C. incubator during the time course. The generation of peroxynitrite is measured at every 30 minutes for 5 hours by automatic robot operation.

Cell injury induced by peroxynitrite after treatment is measured by Alamar Blue stain as described in Example 2.A.3.

2. Results

The data is reported as arbitrary fluorescence unit of Rhodamine 123. Results are mean+SD of net intracellular fluorescence unit, e.g., fluorescence in the presence of cytotoxic compound (AA, KCN or IAA) minus fluorescence without cytotoxic compound (HBSS only) in triplicate. Comparisons among groups are statistically evaluated by two-tailed t-test (Graphpad prism Software, version 2.0). Differences are considered significant at $P<0.05$.

Example 2.C.
Chemical Ischemia: Antimycin A (AA) Treatment

AA is an inhibitor of the mitochondrial cytochrome bc1 complex and inhibits cellular respiration in a dose-dependent manner. Suzuki et al. (1998) *Biochem. Biophys. Res. Commun.* 249:542–545.

Energetically competent cells are seeded onto 96-well plates at $1 \times 10^3$/well or $2.5 \times 10^3$/well as passage 15. The cells are grown in DMEM with 10% FBS and 1.5 g/L sodium bicarbonate for 24 or 48 hours to reach 85% confluence. The cells are washed once with HBSS and then 100 μl of HBSS containing different concentration of AA (Sigma Chemical Co., Cat # A 8674) is added to the cells. AA is dissolved in DMSO to make a stock solution of 50 mM, then diluted with HBSS to 100, 50, 25, 12.5, 6.25, 3.125, and 1.56 μM for dose-response curves. The cells, with or without AA, are incubated at 37° C. in a 5% $CO_2$ humidified incubator for 1, 3, and 5 hours. The concentration of AA is chosen to induce 75% or 100% cell death as a screening dose to test the effect of tocopherols to protect against AA-induced cell toxicity. The concentration of agents used for screening will be dependent upon the agents. Certain control groups contain 100 μl of HBSS only.

The cell toxicity is evaluated at the end of treatment. The cytotoxicity is measured, for example, by SYTOX (Molecular Probe), Live/Dead Viability/Cytotoxicity Kit (Calcein AM/Ethidium Homodimer-1, Molecular Probe), Alamar blue (Accumed), or LDH assay (Sigma Chemical Co.), as described herein.

Example 2.D
Chemical Ischemia: 2,4,-Dinitrophenol (DNP) Treatment

Energetically competent cells are seeded onto 96-well plates at $1 \times 10^3$/well or $2.5 \times 10^3$/well as passage 15. The cells are grown in DMEM with 10% FBS and 1.5 g/L sodium bicarbonate for 24 or 48 hours to reach 85% confluence. The cells are washed once with HBSS and 100 μl of HBSS containing different concentration of 2,4-Dinitrophenol (DNP) (Sigma Chemical Co., Cat # D 7004) is added to the cells. DNP is dissolved in DMSO to make a stock solution of 100 mM, then further diluted with HBSS to 1000, 500, 250, 125, 62.5, 31.25, 15.6, and 7.8 μM for dose-response curves. The cells, with or without DNP, are incubated at 37° C. in a 5% $CO_2$ humidified incubator for 1, 3, and 5 hours. The concentration of DNP is chosen to induce 75% or 100% cell death as a screening dose to test the effect of tocopherols to protect against DNP-induced cell toxicity. The concentration of tocopherols used for screening will be dependent upon the tocopherols. Certain control groups contain 100 μl of HBSS only.

The cell toxicity is evaluated at the end of treatment. The cytotoxicity is measured, for example, by SYTOX (Molecular Probe), Live/Dead Viability/Cytotoxicity Kit (Calcein AM/Ethidium Homodimer-1, Molecular Probe), Alamar blue (Accumed), or LDH assay (Sigma Chemical Co.), as described herein.

Example 2.E.

Chemical Ischemia: Sodium Iodoacetate (IAA) Treatment

The metabolic inhibitor IAA is a powerful alkylating agent that binds to the active site of glyceraldehyde 3-phosphate dehydrogenase and irreversibly inhibits the action of this enzyme to induce ATP depletion. Gore et al. (1989a) *J. Clin. Invest.* 83:386–396; Gore et al. (1989b) *Am. J. Physiol.* 257:C347–C354. Energetically competent cells are prepared and are seeded onto 96-well plates at $1\times10^3$/well or $2.5\times10^3$/well as passage 15. The cells are grown in DMEM with 10% FBS and 1.5 g/L sodium bicarbonate for 24 or 48 hours to reach 85% confluence. The cells are washed once with HBSS and then 100 μl of HBSS containing different concentration IAA (Sigma Chemical Co., Cat # I-2512) is added to the cells. IAA is dissolved in HBSS to make a stock solution of 10 mM, then further diluted with HBSS to 200, 100, 50, 25, 12.5, 6.25, 3.125, and 1.56 μM for dose-response curves. The cells, with or without IAA, are incubated at 37° C. in a 5% $CO_2$ humidified incubator for 1, 3, and 5 hours. The concentration of IAA is chosen to induce 75% or 100% cell death as a screening dose to test the effect of tocopherols to protect against IAA-induced cell toxicity. The concentration of agents used for screening will be dependent upon the agents. Certain control groups contain 100 μl of HBSS only.

The cell toxicity is evaluated at the end of treatment. The cytotoxicity is measured, for example, by SYTOX (Molecular. Probe), Live/Dead Viability/Cytotoxicity Kit (Calcein AM/Ethidium Homodimer-1, Molecular Probe), Alamar blue (Accumed), or LDH assay (Sigma Chemical Co.), as described herein.

Example 2.F

Assessment of Cell Viability

1. LDH Measurement

The hypoxia/reoxygenation or chemicals-induced cell toxicity is evaluated by measuring lactate dehydrogenase (LDH) activity released into the bathing medium. 50 μl of HBSS collected from each well is added to a 96 well plate and then mixed with 100 μl reagent from LD-L 20 Kit (Sigma, Cat # 228-20). The plate is immediately placed into the SpectraMax 340 and read at 340 nm wavelength at 25° C. for 3 minutes at 30 seconds intervals (kinetic measurement). All of the sample readings subtract the background readings, which is 50 μl HBSS and 100 μl of assay reagent. LDH activity (units/liter) is calculated by kinetic Softmax PRO software, one unit of LDH activity is defined as that amount of enzyme that catalyzed the formation of one micromole of NADH per minute under the condition of the assay procedure. All data is expressed as mean±S.D. from duplicates for 4 culture wells. A paired t-test is performed comparing treated groups: (Toxin+Tocopherol) with non-treated groups (Toxin only) after subtracting the control groups (HBSS only) for each data set. Comparisons among groups are statistically evaluated by two-tailed t-test (Graphpad prism Software, version 2.0). Differences are considered significant at P<0.05.

2. Alamar Blue Measurement

Alamar blue, an oxidation-reduction sensitive dye, is a fluorometric/colorimetric indicator of metabolic activity. Alamar Blue is non-toxic dye, making it possible to obtain measures of the metabolic rate and the maximal functional capacity of mitochondrial in living cells. At the 4 hour incubation time point, 20 μl of 1xAlamar Blue is added to each well and incubated for 60 minutes prior to measurement. The plates are read on a cytofluorometer at 540 nm excitation and 590 nm emission to determine the conversion of the colorimetric dye to a fluorometric reading. The data is compared to non-treated cells (control) and is expressed as mean±S.D from 4 culture wells. Alamar Blue fluorescence units obtained from each group will subtract that from cell-free wells with only HBSS and fluorescence reagent. Data are represented as mean±SD. A paired t-test is performed comparing treated groups (Toxin+Tocopherol) with non-treated groups (Toxin only) after subtracting the control groups (HBSS only) for each data set. Comparisons among groups are statistically evaluated by two-tailed t-test (Graphpad prism Software, version 2.0). Differences are considered significant at P<0.05.

3. SYTOX Measurement

SYTOX Green nucleic acid stain is a high-affinity nucleic acid stain that easily penetrates cells with a compromised plasma membrane but will not cross the membrane of live cells. The nucleic acids of dead cells fluoresce bright green at 524 nm when excited with the 488 nm spectral source or with any other 450–500 nm source. Hence during a time course with cells incubated with SYTOX, the fluorescent emission at 524 nm is proportional to cell death. In the cell viability assay chemical ischemia is created in cells that are incubated with the SYTOX dye. The compound antimycin is used to simulate ischemia at the same time as stimulating the cells with forskolin. Antimycin inhibits electron transport from $FADH_2$ between complexes II and III and hence lowers cellular ATP synthesis. The assay is performed on cells grown in 96-well format allowing high throughput screening of compounds.

Materials: (i)SYTOX Green dye, supplied as a 5 mM solution in DMSO (Molecular Probes # S-7020) is stored at −20° C. until use. ii.) Antimycin-A: (Sigma # A-8674) dissolve 5.28 g in 10 ml of DMSO to make a 10 mM stock solution. Aliquot at 100 μl. This 10 mM stock is then diluted to 1 mM with DMSO and aliquoted at 25 μL. Both the 10 mM and the 1 mM are stored at −20° C. until use. (iii) Forskolin (Sigma # F-6886), dissolve 50 mg aliquot in 1.62 ml of DMSO to make a 100 mM stock solution. Aliquot at 100 μl and store at −20° C. until use. iv.) HBSS-SYTOX-FORSKOLIN-ANTIMYCIN (H-S-F-A) solution: H-S-F-A solution is made up fresh prior to each assay in sterile 175 ml or 225 ml Falcon bottles. The working concentrations for the assay are 3 μM SYTOX, 50 μM Forskolin and 30 μM Antimycin.

In each experiment, a 1:500 dilution with HBSS from the 500 μM stock solution is made to generate a 1 μM final working solution of SYTOX Green. The final concentration of DMSO is 0.2%.

Cells are grown in in 96-well black plates (with or without clear bottoms) at a density of 1000 cells per well for 24 hours. The necessary number of 96-well plates containing the specific cell type are obtained and placed in the laminar flow safety cabinet. A sterile microtiter basin is filled with the appropriate volume of pre-warmed 1xHBSS. Using aseptic technique and an 8-channel aspirator, the media is carefully removed from the cells and replaced with 200 μl of 1xHBSS. This is done as quickly as possible to prevent the cells drying out. The plates are then placed in the humidified 37° C. incubators of the Biomek 2000 Side Loader. Four plates are washed at a time so as to minimize the time that the cells are sitting in 1xHBSS prior to addition of the H-S-A-compound test solution.

Compound(s) are mixed with the 1 μM SYTOX working solution and added to the washed cell culture wells. Fluorescence is measured at designated time points (488 nm excitation and 530 nm emission). All of the sample readings subtract the background readings, which is cell-free wells only containing HBSS buffer with SYTOX green dye. The data is compared to non-treated cells (control) and is expressed as mean±S.D. from 4 culture wells. SYTOX Green fluorescence units obtained from each group are corrected for basal fluorescence (cell-free wells with only HBSS and fluorescence reagent). Data are represented as mean±SD. A paired t-test is performed comparing treated groups (Toxin+Agent) with non-treated groups (Toxin only) after subtracting the control groups (HBSS only) for each data set.

Comparisons among groups are statistically evaluated by two-tailed t-test (Graphpad Prism Software, version 2.0). Differences are considered significant at P<0.05.

4. Live/Dead Viability/Cytotoxicity Measurement

The Live/Dead Viability/Cytotoxicity Kit (Molecular Probes, Calcein AM/Ethidium Homodimer-1, Molecular Probe, Cat # L 3224) provides a single-step, two color assay which measures both live and dead cells at same time point. The live cells are identified by intracellular esterase activity, and dead cells are identified by the lack of plasma membrane integrity. The cell-permeant esterase substrate Calcein AM is nonfluorescent converted by enzymatic activity to highly fluorescent Calcein, which is retained within live cells and imparts an intense green fluorescence. Ethidium homodimer-1 (EthD-1) is a dye excluded from cells with intact membrane but is readily able to enter dead cells undergoes a fluorescence enhancement upon binding nucleic acids, producing a bright red fluorescence. At the end of reoxygenation or chemical ischemia treatment. 100 µl of HBSS containing Calcein AM (2 µM) and EthD-1 (4 µM) are added to each well yielding 200 µl per well containing 1 µM Calcein AM and 2 µM EthD-1. The samples are incubated at room temperature for 15 minutes prior to measurement of fluorescence at 485 nm excitation and 530 nm emission for living cells and at 485 nm excitation and 645 nm emission for dead cells. All of the sample readings will subtract the background readings, which is cell-free wells only containing HBSS buffer and Calcein AM/EthD-1. The data is compared to non-treated cells (control) and is expressed as mean±S.D from 4 culture wells. Calcein/EthD-1 fluorescence units obtained from each group will subtract that from cell-free wells with only HBSS and fluorescence reagent. Data are represented as mean±SD. A paired t-test is performed comparing treated groups (Toxin+Tocopherol) with non-treated groups (Toxin only) after subtracting the control groups (HBSS only) for each data set. Comparisons among groups are statistically evaluated by two-tailed t-test (Graphpad prism Software, version 2.0). Differences are considered significant at P<0.05.

Example 2.G

Hypoxia/Reoxygenation Treatment

Oxidatively competent cells are prepared as described in Example 1.

The cells are washed once with 1×HBSS and 100 µl of HBSS is added. Agents to be tested are diluted in HBSS and added to the cells. Control cell groups have only HBSS added. Cells are plated in a modular incubator chamber (Billups-Rothenberg Inc., Del Mar, Calif.) and flushed for 15 minutes with 95% N2/5% $CO_2$ (14 L/ml) to reach to the environmental oxygen concentration toward zero. The chamber is sealed and placed into a 37° C. incubator for various times. The cells incubated under normoxic conditions from the same batch and passage will be used as normoxic controls. "Normoxic condition" refers to standard cell culture with the use of 90% air (21.8% oxygen) and 5% $CO_2$.

Reoxygenation is attained by removing the cell culture plates from the chamber and replacing cultures in normoxic conditions for various times. The positive control drug Trolox (10 µM) or N-acetylcystein (NAC), an antioxidant, will be used in each experiment.

Cell toxicity is evaluated at the end of treatment. The cytotoxicity is measured, for example, by SYTOX (Molecular Probe), Live/Dead Viability/Cytotoxicity Kit (Calcein AM/Ethidium Homodimer-1, Molecular Probe, Cat # L 3224), Alamar blue (Accumed), or LDH assay (Sigma, Cat # 228-20), as described herein.

Example 3

Example 3 describes organ-based assays for determining the efficacy of a cytoprotective tocopherol. Such protocols can be used, for example, to re-test tocopherols found to be effective in cellular assays, such as those described in Example 2.

Example 3.A

Isolated Rat Heart

This organ perfusion procedure is useful for testing tocopherols found to counteract ischemia in cell-based assays. Because ischemia can rapidly result in disruptions in how cells make and regulate energy synthesis, compounds or mixtures identified through cell-based screening that protect against energetic disturbances may be used in methods of treatment and prevention of myocardial ischemia and reperfusion injury.

Investigations of myocardial ischemia have been undertaken using a broad range of experimental models. The cytoprotective effect of a tocopherol may be tested in the experimental setting, where its eventual coronary effects can be controlled and separated from its direct metabolic and molecular effects on the myocyte. Several endpoints may be employed to test the occurrence of cytoprotection. For example, utilized parameters include, but are not limited to, the following: (1) reduction in the extent of myocardial infarct size; (2) improvement in mechanical and/or metabolic function; (3) substrate utilization; (4) release of lactate; (5) tissue content of high energy stores; (6) isolated mitochondrial function; (7) integrity of cellular or intracellular membranes; (8) adenosine and purine metabolism; (9) oxygen toxicity, and (10) release of intracellular substances. Among various models, the isolated and perfused heart preparation is widely used in testing different agents classified as cardioprotective by using these endpoints. This system allows the examination of experimental cardiac ischemia and reperfusion injury without the complications of an intact animal model. The principle of the model is based on forcing blood or an oxygenated fluid into the coronary arteries through a cannula implanted in the aorta. This protocol is designed to assess the effects of a tocopherol, or mixture of tocopherols, on normal, nonischemic, isolated rat hearts and on the recovery of these hearts undergoing global ischemia.

1. Procedure

Male Sprague-Dawley rats (250–300 g, 6–10 weeks of age) are fasted overnight and then anaesthetized with 3% isoflurane and heparinized with 200 units of 1,000 units/mL of heparin by an intravenous injection. Following induction of anesthesia, the chest and upper abdomen are shaved and swabbed with an antiseptic (e.g., Betadine, or equivalent). 0.2 mL of 1,000 units/mL of heparin is administered through the penis vein. After waiting one minute for heparinizing, the skin is incised by a longitudinal cut from the middle of the upper abdomen to the throat. The abdomen is opened up to the diaphragm and the diaphragm cut off the ribs following the anterior part of the inferior thoracic aperture. The thorax is cut open on the left and right side following the bone-cartilage-border on a line parallel to the sternum starting at the diaphragm and proceeding as far cranial as to the first rib. The complete anterior thoracic wall is turned upwards over the animal's head and fixed in this position by two towel clamps. The pericardium is removed as far as its attachment at the vascular stem. The heart is slightly elevated, cut out with a pair of bent scissors, and rapidly placed into ice-cold Krebs-Henseleit buffer solution (KH, 118 mM NaCl, 4.7 mM KCl, 1.2 mM $MgSO_4$, 1.2 mM $KH_2PO_4$, 11 mM glucose, 25 mM $NaHCO_3$, and 2 mM $CaCl_2$). After the contractile activity of the heart has completely ceased, the heart is trimmed and the ascending aorta freed from the connective tissue. The aorta is cannulated, and the heart mounted on a non-recirculation Langendorff perfusion apparatus (Radnoti Glass Technology, Inc.). The heart is perfused in a retrograde fashion via the aorta at a constant pressure of 100 cm $H_2O$ with KH solution oxygenated with 95% $CO_2$ and 5% $CO_2$ to maintain pH 7.4 at 37° C. To assess contractile function, a latex balloon; is inserted into the left ventricular cavity through the mitral orifice and connected to a pressure transducer by a rigid polyethylene tubing. The balloon is inflated with water to a left ventricular end-diastolic pressure (LVEDP) of 1 to 10 mm Hg. The sinus node is removed by cutting the right atrium and the heart paced to 300 beats/min at 3–5 V using an external pacemaker, ensuring identical heart rates for all hearts. After a 30 minute aerobic perfusion for equilibration, the heart is subjected to complete global ischemia for 30 minutes by turning off the perfusion system. After 30 minute ischemia, the perfusion system is restarted, and the heart reperfused for an additional 60 minutes. Tested tocopherols are administered to the heart by adding them to the KH buffer during pre-ischemia period, or pre-ischemia and reperfusion period. The left ventricular systolic pressure (LVSP), the LVEDP, the left ventricular developed pressure (LVDP), the first derivative of the rise and fall in the left ventricular pressure (dp/dt max, dp/dt min) and heart rate are automatically recorded using a computer and a software. The coronary effluent during reperfusion is collected and the lactic dehydrogenase (LDH) measured spectrophotometrically using a microplate reader.

2. Statistical Model

The statistical parameters used to select the number of animals required for statistical significance are based upon estimated variation. The parameters are: power=0.8; significance=0.05; coefficient of variation of the sample mean=100%, and detection threshold=1 standard deviation. The equation used to estimate the number of animals required is: $n \geq 2 (\sigma/\delta)^2 (t_{\alpha[df]} + t_{2(1-P)[df]})$. A two-tailed comparison was chosen to allow comparison between experimental groups, as well as comparison to the control group.

The data collected from the technique development group of animals are used to validate the assumed variance. The number of animals in subsequent groups are adjusted accordingly.

| Group | Animals/Dose | Doses | No. Compounds Examined | Total No. Animals |
|---|---|---|---|---|
| Control (untreated) | 16 | 1 | n/a | 16 |
| experimental | 16 | 3 | 9 | 432 |

| Group | Animals/Dose | Doses | No. Compounds Examined | Total No. Animals |
|---|---|---|---|---|
| technique development | — | — | — | 32 |
| Total animals | | | | 480 |

3. Data Analysis

This protocol measures the recovery from ischemia and reperfusion injury of contractile function in hearts treated with putative cytoprotective tocopherols. Comparison of each experimental group with the control group is performed via the Student-Newman algorithm or by ANOVA. The data is inspected to confirm the underlying assumptions of the comparison algorithms: normality, equal samples size, etc. Additionally, outliers in the data are inspected and diagnosed through comparison with the laboratory notes. Additionally, the performance of experimental groups are compared relative to each other. These comparisons are also performed using the Student-Newman algorithm or multiple regression ANOVA, as above.

Example 3.B
Isolated Perfused Rat Liver

This organ perfusion procedure is useful for testing tocopherols found to be useful in cell-based assays. Because ischemia can rapidly result in disruptions in how cells make and regulate energy synthesis, tocopherols or mixtures identified through cell-based screening that protect against energetic disturbances may be used in methods of treatment and prevention of hypothermic metabolic arrest and subsequent rewarming injury. Tocopherols characterized for this use may also be of use in methods of treatment of other ischemic disorders such as stroke and heart attack.

The isolated perfused rat liver model is a gold-standard model employed by investigators for the study of liver transplantation. It is well-established, characterized, and experimental endpoints are well-defined for graft function. Standard variables associated with hepatic function are measured and include oxygen extraction, enzyme leakage, and alterations in portal venous resistance. Histological assessment is also obtained. These measurements characterize hepatic function with regards to physiologic, cellular and morphologic assessment.

1. Procedure

Male Sprague-Dawley rats (250–300 g, 6–10 weeks of age) are fasted overnight and then anaesthetized as described in Example 3A. Following shaving of the abdomen, abdominal contents are exposed thorough an ~2.5 cm midline laparotomy. 200 units of 1,000 units/mL of heparin is administered through the infrarenal inferior vena cava. A 5-O silk ligature is placed about (not tied) the portal vein and the suprarenal inferior vena cava. The portal vein is cannulated with a modified 16 gauge angiocatheter and secured. With care to avoid air emboli, the liver is perfused in situ during the hepatectomy interval at a flow rate of 2.5–3.0 mL/g liver minute (about 20 mL/minute) with 35° C. modified Krebs-Henseleit buffer containing 119 mM NaCl, 20 mM $NaHCO_3$, 4.7 mM KCl, 1.2 mM $KH_2PO_4$, 1.2 mM $MgSO_4$ and 2 mM $CaCl_2$, oxygenated with 95% $O_2$:5% $CO_2$. Immediately following the initiation of perfusion, the abdominal aorta and infrarenal inferior vena cava are transected, the thoracic cavity entered, and right atrium incised. Following ligation of the suprarenal inferior vena cava with a 5-O silk ligature, a ligature is placed about (not tied) the thoracic inferior vena cava proximal to the right hemidiaphragm. A modified 14 h angiocatheter is inserted distally through the incised right atrium and secured. The liver is then sequentially dissected from the diaphragmatic attachments, vascular and visceral pedicles, weighed, and immediately connected to an immersion-thermostated non-pulsatile (hydrostatic) perfusion system. Ischemia time is typically anticipated to be <60 seconds, with a total surgical procedures time of 5–7 minutes. Animals are effectively euthanized during the procedure under full general anesthesia by terminal bleed. This is achieved by transection of the abdominal inferior vena cava and aorta, followed by thoracotomy.

Following hepatectomy, livers are equilibrated in Krebs-Henseleit buffer at 37° C. for 15 minutes. Pre-storage assessment of organ function includes: (i) measurement of portal venous resistance; (ii) visual inspection for gas emboli; and (iii) oxygen extraction. Following assessment, livers are removed from perfusion system, flushed with 20 mL of test storage solution at 4° C. at a rate of 2 mL/minute. Following hypothermic equilibration in test storage solution, inflow and outflow cannulas are occluded, and the organ is stored at 4° C. in 40×80 mm crystallization dishes for predetermined time intervals.

Liver viability is assessed following hypothermic storage by reperfusion at 37° C. with modified Krebs-Henseleit buffer containing 119 mM NaCl, 20 mM $NaHCO_3$, 4.7 mM KCl, 1.2 mM $KH_2PO_4$, 1.2 mM $MgSO_4$, and 2 mM $CaCl_2$, oxygenated with 95% $O_2$:5% $CO_2$. at a flow rate of approximately 3 mL/g liver/minute. Oxygen extraction is determined by the Fick principle, and assessed 30 and 60 minutes following rewarming-reperfusion. Aliquots of hepatic perfusate outflow are collected and assayed for lactate dehydrogenase release. Additional measurements include assessment of post storage portal venous resistance and histological assessment of tissue by H&E staining.

The statistical parameters used to select the number of animals required for statistical significance are as described in Example 3.A.

2. Data Analysis

This protocol assesses oxygen consumption in organs treated with putative cytoprotective tocopherols and with control compounds. Comparison of each experimental group with the control group is performed via the Student-Newman algorithm or by ANOVA. The data is inspected to confirm the underlying assumptions of the comparison algorithms: normality, equal samples size, etc. Additionally, outliers in the data are inspected and diagnosed through comparison with the laboratory notes. Additionally, the performance of experimental groups are compared relative to each other. These comparisons are also performed using the Student-Newman algorithm or multiple regression ANOVA, as above.

Example 3.C

Rat Heart Hypothermic Preservation

This example outlines procedures of rat heart hypothermic storage with the supplemental use of cardioplegia to obtain satisfactory myocardial preservation for heart transplantation. One of the most fundamental aspects of myocardial preservation during transplantation is the utilization of hypothermia. The beneficial effects of supplementing hypothermia with cardioplegia during the various stages of heart procurement and implantation have been documented, and, thus, this procedure has become standard practice in clinical transplantation.

Heart preservation: 250–300 g male Sprague-Dawley rats are anaesthetized with 3% isoflurane and heparinized with 200 units of 1,000 units/ml of heparin intravenous injection. The thorax is opened and the heart rapidly excised and placed in ice-cold Galileo's agent or vehicle in St. Thomas' cardioplegic solution. The blood is flushed out with 15 ml of cold Galileo's agent or vehicle in St. Thomas' cardioplegic solution via the ascending aorta. The heart is then stored in 100 ml of cold Galileo's agent or vehicle in St. Thomas' cardioplegic solution for 12 hours at 4° C.

Measurement of cardiac function: The heart contractile ability is tested by isolated perfused (Langendorff) heart method, as described herein. After 12 hours storage, the heart is mounted on a non-recirculation Langendorff perfusion apparatus (Radnoti Glass Technology, Inc.) by cannulating the aorta. The heart is perfused in a retrograde fashion via the aorta at a constant pressure of 100 cm $H_2O$ with Krebs-Henseleit buffer solution (KH) containing of 118 mM NaCl, 4.7 mM KCl, 1.2 mM $MgSO_4$, 1.2 mM $KH_2PO_4$, 11 mM glucose, 25 mM $NaHCO_3$ and 2 mM $CaCl_2$, oxygenated with 95% $O_2$ and 5% $CO_2$ to maintain pH 7.4 at 37° C. To assess contractile function, a latex balloon is inserted into the left ventricular cavity through the mitral orifice and connected to a pressure transducer by a rigid polyethylene tubing. The balloon is inflated with water to a left ventricular end-diastolic pressure (LVEDP) of 1 to 10 mm Hg. The heart is perfused for 45 minutes. The left ventricular systolic pressure (LVSP), the LVEDP, the left ventricular developed pressure (LVDP), the first derivative of the rise and fall in the left ventricular pressure (dp/dt max, dp/dt min) and heart rate are automatically recorded using a computer and a software. The LVDP, LVEDP, dp/dt max, heart rate and heart function index (LVDP×heart rate) between experimental groups are compared using Student t test and a p value of less than 0.05 will be considered to indicate statistical significance.

Example 4

Rat Heart Infarct Size Assay

Animal-based assays are used to determine efficacy of cytoprotective tocopherols. Animal-based assays can be used, for example, with agents found to be effective in at least one cellular assay (such as those described in Example 2) and/or an organ assay (such as those described in Example 3).

This assay is used to assess the efficacy of cytoprotective tocopherols in protecting heart muscle against necrosis during myocardial infarction induced in rats.

1. Procedure

250–300 g male Sprague-Dawley rats are anaesthetized initially with 3% isoflurane and the concentration of isoflurane is reduced to 1.25% after orotracheal intubation. Intubation is performed with a modified Teflon 16-gauge×2" intravenous catheter (Abbott) by transillumination and the rats are ventilated by a small animal ventilator (Harvard) with a tidal volume of 10 ml/kg and respiratory rate 75 breaths/min. The animal is placed supine and core body temperature, monitored by a rectal thermometer, is maintained at 37° C. by using a heating blanket (Homeothermic Blanket System Harvard). The operation areas are cleaned with alcohol swab and a craniocaudal incision approximately 2.5 cm is made, parallel with and slightly to the left of the sternum, through the skin and pectoral muscles, to expose the ribs. A blunt curved forceps is plunged between the forth and fifth ribs, through the intercostal muscles, at a point approximately 2 mm to the left of the sternum and the gap widened to about 15 mm. The fifth costal cartilage is transected with a scissors at about 0.5 cm to the left of the sternum, the pericardium opened and the heart exteriorized by applying pressure to the lateral aspects of the thoracic cage. A 6-0 silk suture with a taper needle is passed around the left coronary artery near its origin, which lies in contact with the left margin of the pulmonary cone, at about 1 mm from the insertion of the left auricular appendage. As the heart is returned to the mediastinum, the ligature is tied with a slip knot and one end of the suture is exteriorized through the chest wall to allow removal of the ligature by traction on the exteriorized portion without re-opening the chest. The chest is closed by 1 to 2 intercostal sutures and then the muscles and skin with 4-0 silk suture. The endotrachial tube is removed and the rats returned to the cage to wake. After 30 minutes when the occlusion is completed, the coronary artery is reperfused by releasing the knot and removing the exteriorized suture without anesthesia and the animal is allowed free access to food and water.

2. Measurement of Infarct Size and Area at Risk

The following day, the rats are re-anesthetized with isoflurane, the coronary artery is again briefly occluded through ligation of a suture at the same site of the previous occlusion, and 2 ml of 5% Even's blue dye is injected into the vena cava to delineate the ischemic area at risk (negative staining with Evan's blue) of the left ventricle. The heart is removed, washed with saline, and cut into four 2-mm thick transverse slices from apex to base. The slices are incubated in 1% triphenyltetrazolium chloride (TTC) in pH 7.4 phosphate buffer for 20 minutes at 37° C. Tetrazolium reacts with NADH in the presence of dehydrogenase enzymes causing viable tissue to stain a deep red color that is easily distinguished from the infarcted pale-unstained necrotic tissue. The areas of infarcted tissue, the risk zone and the whole left ventricle are determined using a computerized image system. The area for each region are averaged from slices. Infarct size is expressed both as a percentage of the total left ventricle and as a percentage of the ischemic risk area.

The statistical parameters used to select the number of animals required for statistical significance are as described in Example 3.A.

Example 5

Efficacy of Various Tocopherols in Ameliorating Alterations in Normal Energy Metabolism Alpha-, delta-, and gamma-tocopherols were tested individually for their ability to counteract disruptions of normal energy metabolism. Both stereoisomers (+ and −) of alpha-tocopherol, and the + stereoisomer of delta-tocopherol were tested. (+)-Alpha-tocopherol Type V comprises mixed isomers (Sigma Chemical Co., Cat #T 3634). (+/−) indicates a mixture of (+) and (−) isomers. Delta-tocopherol was obtained from Sigma Chemical Co. (Cat#T2028). Gamma-tocopherol was obtained from Sigma Chemical Co. (Catalog No. T1782).

Stocks of tocopherols (about 40 mg/ml) were prepared by mixture with 10 mM glycocholic acid. (Glycocholic acid does not protect cells at the concentrations used.) Oxidatively competent cells were treated simultaneously with a tocopherol and mitochondrial poison antimycin A (as described in Example 2.C). Cell death after 4 hours of treatment was measured by SYTOX assay, as described in Example 2.F. (Experiments described in the Examples below were performed in generally the same way

TABLE 1

| | Cell Death (%) | | | | |
|---|---|---|---|---|---|
| Dose ($\mu$g/ml) | + gamma-tocopherol | (+/−) alpha-tocopherol | (+) alpha-tocopherol Type V | (+) alpha-tocopherol | (+) delta-tocopherol |
| 100 | −8.5 ± 3.3 | 19.7% ± 2.9 | 35.8% ± 9.8 | 33.78% ± 1.5 | −68.19% ± 25.2 |
| 33 | 16.7 ± 1.9 | 44.2% ± 1.2 | 45.06% ± 7.7 | 49.8% ± 6.0 | −8.19% ± 1.4 |
| 11 | 37.2 ± 0.7 | 52.4% ± 3.4 | 70.77% ± 8.3 | 64.4% ± 3.1 | 21.3% ± 1.0 |
| 3.7 | 69.3 ± 3.3 | 73.5% ± 1.2 | 72.0% ± 2.0 | 70.13% ± 5.8 | 39.3% ± 3.8 |
| 1.2 | 76.8 ± 3.1 | 77.2% ± 0.8 | 72.7% ± 5.4 | 77.0% ± 2.5 | 61.3% ± 4.2 |

± SD, Standard deviation.

The data presented above show that all the tocopherols tested were capable of ameliorating stress secondary to inhibition of energy metabolism in a concentration- or dose-dependent manner, as manifested by cell death. Of the tocopherols, delta-tocopherol and gamma-tocopherol were the most potent.

Example 6

Effect of Various Salts on Efficacy of Tocopherols

Various salts of (+)alpha-tocopherol were tested for potency, including nicotinate, phosphate and succinate.

TABLE 2

| | Cell Death (%) | | | |
|---|---|---|---|---|
| Dose of tocopherol ($\mu$g/ml) | alpha-tocopherol acetate | alpha-tocopherol nicotinate | alpha-tocopherol phosphate | alpha-tocopherol succinate |
| 100 | 38.% ± 2.3 | 67.5 ± 2.8 | 43.2 ± 17.4 | 98.7 ± 6.0 |
| 33 | 64.8% ± 4.9 | 77.5 ± 3.0 | 47.2 ± 10.8 | 90.4 ± 7.4 |
| 11 | 71.1% ± 1.5 | 74.0 ± 2.4 | 83.9 ± 4.4 | 85.5 ± 2.5 |
| 3.7 | 77.5% ± 4.9 | 76.8 ± 7.0 | 76.5 ± 4.2 | 83.9 ± 0.3 |
| 1.2 | 73.2% ± 3.3 | 81.0 ± 2.5 | 79.7 ± 8.7 | 85.8 ± 1.4 |

± SD, Standard deviation

As shown above, the acetate salt of alpha-tocopherol demonstrated a higher efficacy (reduction of cell death to 38%) than the other salts of alpha-tocopherol.

Example 7
Synergistic Mixture of Isomers of Tocopherol for Use as Cytoprotectants Various concentrations of alpha- and gamma-tocopherol were tested for a synergistic ability to counteract disruptions of normal energy metabolism. As exemplified below, such assays are useful for the identification of combinations of compounds with synergistic activity. In general, as described above, a combination of compounds is considered to exhibit "synergistic" cytoprotective activity, if the protection afforded by the combination is greater than the additive effect provided by the agents alone (in comparison to a control sample lacking a test compound). In other words, the combination exhibits activity as a non-linear multiple of the activities of the individual compounds. It is appreciated that, provided with the teachings of the present invention, the practitioner will be able to select concentration ranges of the identified compositional components and test such components in an appropriate cell or tissue protection assay, such as one or more of those exemplified herein. The test paradigm will optimally include a "grid" of concentrations of each component tested alone and in combination, and will include untreated control test conditions as well.

Combinations of the stereoisomers (+and −) of alpha-tocopherol were tested in combination with gamma tocopherol. Gamma- and alpha-tocopherol were individually not very effective; cell death was 62.5% for gamma-tocopherol at 1 $\mu$g/ml and 53% for alpha-tocopherol at 10 $\mu$g/ml (the highest concentrations tested). Certain concentrations of (+/−) alpha tocopherol and gamma-tocopherol exhibited synergistic effects (e.g., 0.33 $\mu$g/ml alpha-tocopherol plus 0.03 $\mu$g/ml gamma-tocopherol; 3.3 $\mu$g/ml alpha-tocopherol with 0.03–0.11 $\mu$g/ml gamma-tocopherol; 10 $\mu$g/ml alpha-tocopherol with 0.03 or 0.33 $\mu$g/ml gamma-tocopherol). Other concentration combinations provided optimized concentrations, where the effects were additive or slightly better than additive. Examples of such optimized combinations include, for example, 0.33 $\mu$g/ml alpha- with 0.11–0.33 $\mu$g/ml gamma-tocopherol; 1.1 $\mu$g/ml alpha- with 0.33 or 1 $\mu$g/ml gamma-tocopherol; 3.3 $\mu$g/ml alpha- with 0.33 $\mu$g/ml gamma-tocopherol; 10 $\mu$g/ml alpha- with 0.11 $\mu$g/ml gamma tocopherol. Thus, the present invention provides synergistic as well as optimized combinations of alpha- and gamma tocopherol.

Example 8
Synergistic Mixture of Tocopherol and Lactoferrin

In accordance with the present invention, various concentrations of alpha-tocopherol Type V and lactoferrin were identified as possessing synergistic ability to ameliorate stress secondary to alterations in energy metabolism. Bovine lactoferrin may be obtained, for example, from Sigma Chemicals (Saint Louis, Mo., cat. # L9507) or DMV International Nutritionals (cat. # 990432-1) and can be diluted in HEPES buffer (HBSS, HEPES based salt solution) for in vitro testing.

In exemplary stress-induced cell death assays, alpha-tocopherol and lactoferrin were individually relatively ineffective, cell death being 50% for the former at 10 $\mu$g/ml and 96% for the latter at 100 $\mu$g/ml. However, combining the two compounds greatly lowered cell death. Even a small amount of lactoferrin (11 $\mu$g/ml) added to alpha-tocopherol (10 $\mu$g/ml) reduced cell death to 32%, a greater than additive effect. The lowest cell death rate, 9.5%, was achieved with the synergistic combination of lactoferrin (100 $\mu$g/ml) and alpha-tocopherol (10 $\mu$g/ml).

A similar experiment was performed using lactoferrin and (+/−)-alpha tocopherol, with similar results, in that at the highest concentrations tested, alpha-tocopherol and lactoferrin individually had little effect, cell death being at 79.4% for the former and 85.9% for the latter at 10 and 100 $\mu$g/ml respectively. In general, the following combinations were identified as synergistic: 0.36 $\mu$g/ml alpha-tocopherol with 100 $\mu$g/ml lactoferrin; 1.1 $\mu$g/ml alpha-tocopherol with 33 or 100 $\mu$g/ml lactoferrin; 3.3 $\mu$g/ml alpha-tocopherol with 11, 33 or 100 $\mu$g/ml lactoferrin; 10 $\mu$g/ml alpha-tocopherol with 11, 33 or 100 $\mu$g/ml lactoferrin.

Additional experiments demonstrated that lactoferrin acts synergistically with gamma-tocopherol.

Example 9
Formulations of Tocopherols and Flavonoids

Various concentrations of tocopherols and flavonoids were tested for the combined ability to ameliorate disruption of energy metabolism secondary to stress. Tocopherols were obtained from Sigma Chemical Co. and stock solutions (about 40 mg/ml) were prepared by mixture with 10 mM glycocholic acid. Glycocholic acid does not protect cells at the concentrations used.

Flavonoids were commercially obtained, generally from Sigma Chemical Co., St. Louis, Mo., and/or Aldrich Chemical Co., Milwaukee, Wis.

In experiments carried out in support of the invention, various concentrations of diosmin and alpha-tocopherol were tested for synergistic ability to ameliorate disruption of energy metabolism secondary to stress. Cells were treated simultaneously with diosmin, alpha-tocopherol and antimycin A. The cells were treated with various low concentrations of diosmin (Sigma Chemical Co., cat. # D3525) and various low concentrations of (+/−) alpha-tocopherol. Diosmin, alpha-tocopherol and antimycin were mixed together before treating cells. Cell viability was measured 4 hours after treatment using SYTOX. Experiments in support of the present invention showed that diosmin exhibits synergism with (+/−) alpha-tocopherol in protecting cells from stress. For example, diosmin in the range of 3.3–100 $\mu$M was not protective by itself, but was synergistic in that range with 10 $\mu$g/ml (+/−) alpha-tocopherol, a concentration at which (+/−) alpha-tocopherol was only slightly (about 15%) protective by itself. Likewise, the combination of disomin (11–100 $\mu$M) with 1.1 $\mu$g/ml (+/−) alpha tocopherol was synergistic. Combinations of 33–100 $\mu$M diosmin formed optimized combinations with 3.3 $\mu$g/ml (+/−) alpha tocopherol. Diosmin alone provided no protection at a concentration of 100 $\mu$M. However, the combination of 100 $\mu$M diosmin and 100 $\mu$g/ml alpha tocopherol greatly reduced cell death, providing about 70% protection against stress-induced cell death, indicating synergism between these components. A combination of 100 $\mu$M diosmin and 11 $\mu$g/ml (+/−) alpha tocopherol was also synergistic.

Additional experiments demonstrated that diosmin and gamma-tocopherol act synergistically. At concentrations ranging from 0.03–0.3 $\mu$g/ml, gamma-tocopherol was not protective by itself; however, in the presence of diosmin (33–100 $\mu$M), synergism was observed. As noted above, diosmin by itself was not effective over this range. Lower concentrations of diosmin (3.3–11 $\mu$M) were also synergistic with 0.1 $\mu$g/ml gamma tocopherol. Optimized formulations were also revealed (for example, 0.03 $\mu$g/ml gamma tocopherol plus 100 $\mu$M diosmin, 1 $\mu$g/ml gamma tocopherol plus 11 $\mu$M diosmin).

Various concentrations of hesperetin and various tocopherols were tested for ability to ameliorate disruptions in energy metabolism secondary to stress. Oxidatively competent cells were treated simultaneously with hesperetin, antimycin A, and (+/−) alpha-tocopherol, (+)-alpha-tocopherol Type V, (+)-alpha-tocopherol, (+)-delta-tocopherol, or (+)-gamma-tocopherol. Cells were treated and cell death was recorded four hours later. At the concentrations used (2 and 50 μM heperitin, 0.22 and 3.6 μg/ml tocopherol), hesperetin and tocopherols are generally ineffective when tested separately. Addition of 50 μM hesperetin to various tocopherols greatly reduced cell death in a synergistic manner. For example, cell death was reduced to 20% with the combination of 50 μM hesperetin and 3.6 μg/ml (+)-alpha-tocopherol or 0.22 μg/ml (+)-gamma tocopherol. Cell death was reduced to 30% with the combination of 50 μM hesperetin and 0.22 μg/ml (+)-delta-tocopherol. The combination of 0.22 μg/ml tocopherol with hesperetin in the range of 2–60 μM was also particularly synergistic. Thus, hesperetin acts synergistically with various tocopherols, including, without limitation, (+/−) alpha-, delta- and gamma-tocopherol.

Optimized formulations comprising biochanin A and a tocopherol were also identified in experiments carried out in support of the invention. When tested individually, about half of the cells died at the highest concentrations of biochanin A and alpha-tocopherol tested. However, the combination of the two compounds was effective, with the greatest reduction in cell death occurring with the combinations of 15 μg/ml biochanin A and 1.0 μg/ml alpha-tocopherol, and 15 μg/ml biochanin A and 3.0 μg/ml alpha-tocopherol.

Additional experiments, not shown, determined the optimal formulation comprising gamma-tocopherol and biochanin A. Compositions comprising 0.11 or 0.33 μg/ml gamma-tocopherol and 15 μg/ml biochanin A allowed a nearly 40% decrease in cell death compared to gamma-tocopherol alone.

Various concentrations of the flavonoid daidzein and (+/−) alpha-tocopherol were tested for an ability to ameliorate disruption of energy metabolism secondary to stress.

Likewise, optimized formulations comprising daidzein and a tocopherol may be selected and formed in accordance with the present invention. Daidzein and (+/−) alpha-tocopherol were individually and jointly tested for efficacy over a wide range of concentrations. When tested individually, over half of the cells died at the highest concentrations of daidzein and (+/−) alpha-tocopherol tested. However, the combination of the two compounds was effective, with the greatest reduction in cell death in this experiment occurring with the combinations of 15 μM daidzein and 1.0, 3.0 or 10.0 μg/ml (+/−) alpha-tocopherol.

While both alpha-tocopherol and (+/−)-alpha-tocopherol were effective in providing protection, additional studies carried out in support of the present invention also determined optimized formulations for daidzein and alpha-tocopherol in preventing cell death in these cells. Optimized formulations comprised 15 μM daidzein and 3.0 or 10.0 μg/ml (+/−) alpha-tocopherol,. and reduced cell death to about 35–37%.

All documents cited herein are incorporated by reference in their entirety.

Although the foregoing invention has been described in some detail by way of illustration and example for purposes of clarity of understanding, it will be apparent to those of skill in the art that certain changes and modifications may be practiced. Therefore, the descriptions and examples should not be construed as limiting the scope of the invention, which is delineated by the appended claims.

What is claimed is:

1. A method for the amelioration of disruption of energy metabolism in cells secondary to stress in a subject in need thereof, comprising administering to the subject a non-naturally-occurring composition comprising a tocopherol selected from the group consisting of beta-, delta- and gamma-tocopherol and combinations and derivatives thereof, and a synergist selected from the group consisting of flavonoid and lactoferrin and combinations or derivatives thereof, wherein the tocopherol and the synergist are present in amounts effective to ameliorate said disruption of energy metabolism in cells secondary to stress.

2. The method according to claim 1, wherein the tocopherol is delta-tocopherol.

3. The method according to claim 1, wherein the tocopherol is gamma-tocopherol.

4. The method according to claim 1, wherein the synergist is in the form of a pharmaceutically acceptable salt.

5. The method according to claim 1, wherein the flavonoid is hesperetin.

6. The method according to claim 1, wherein the flavonoid is diosmin.

7. The method of claim 1 wherein said flavonoid comprises a combination of hesperetin and quercetin.

8. The method according to claim 1, wherein the flavonoid is lactoferrin.

9. The method according to claim 1, wherein the stress is induced by an environmental alteration, chemical insult or physiological condition.

10. The method of claim 9, where the environmental alteration is hypothermia, hyperthermia, hypoxia or ionizing radiation.

11. The method of claim 9, where the chemical insult is drug toxicity, chemotherapy, exposure to at least one toxin or cell culture.

12. The method of claim 9, where the physiological condition is physical exertion, aging, pre-surgical preparation or post-surgical conditions.

13. The method of claim 9, wherein the subject is an individual.

14. The method of claim 13, wherein the individual is a mammal.

15. The method of claim 14, wherein the mammal is a human.

16. The method according to claim 3, wherein the synergist is hesperetin.

17. The method according to claim 16, wherein the composition further comprises quercetin.

18. The method according to claim 3, wherein the synergist is quercetin.

19. The method according to claim 3, wherein the composition further comprises delta-tocopherol.

20. The method according to claim 1, wherein the tocopherol is beta-tocopherol.

21. The method according to claim 1, wherein the synergist is quercetin.

22. The method according to claim 1, herein the synergist is diosmin.

* * * * *